United States Patent [19]

Takehiko et al.

[11] Patent Number: 5,032,594
[45] Date of Patent: Jul. 16, 1991

[54] TRICYCLIC FUSED PYRIMIDINE DERIVATIVES, THEIR PRODUCTION AND USE

[75] Inventors: Naka Takehiko, Kobe; Nagaoka Akinobu, Kawanishi, both of Japan

[73] Assignee: Takeda Chemical Industries, Ltd., Osaka, Japan

[21] Appl. No.: 480,585

[22] Filed: Feb. 15, 1990

[30] Foreign Application Priority Data

Feb. 15, 1989 [JP] Japan .................................. 1-037126
Oct. 24, 1989 [JP] Japan .................................. 1-277386
Jan. 8, 1990 [JP] Japan ...................................... 2-2215

[51] Int. Cl.$^5$ .................... A61K 31/505; C07D 487/14
[52] U.S. Cl. ..................... 514/267; 544/251; 540/562; 514/220
[58] Field of Search ............ 544/251; 540/562; 514/220, 267

[56] References Cited

U.S. PATENT DOCUMENTS

| | | | |
|---|---|---|---|
| 3,915,976 | 10/1990 | Selmond | 544/253 |
| 4,603,203 | 7/1986 | Furukawa et al. | 544/262 |
| 4,824,848 | 4/1989 | Naka et al. | 514/258 |
| 4,912,104 | 3/1990 | Naka et al. | 514/220 |

FOREIGN PATENT DOCUMENTS

32972 9/1976 Japan .

OTHER PUBLICATIONS

Central Patents Index, Basic Abstracts Journal, Section B, 32972A/18 (Japanese Patent Publication Laid Open No. 31694/1978).

Primary Examiner—Mukund J. Shah
Assistant Examiner—Matthew V. Grumbling
Attorney, Agent, or Firm—Wegner, Cantor Mueller & Player

[57] ABSTRACT

Novel tricyclic fused pyrimidine derivatives of the formula (I):

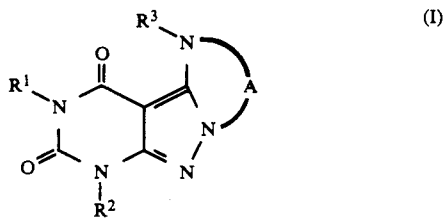

wherein either one of $R^1$ and $R^2$ is hydrogen or an optionally substituted aralkyl group and the other is hydrogen, an optionally substituted aralkyl group or an aliphatic hydrocarbon group; $R^3$ is hydrogen, an aliphatic hydrocarbon group or acyl group; and A is an optionally substituted divalent hydrocarbon chain having 2 to 4 carbon atoms and salts thereof are strong adenosine antagonists and activate cerebral functions and metabolisms, thus being useful as therapeutic or prophylactic agents for neurological or psychic changes caused by cerebral apoplexy, brain injury or cerebral atrophy.

34 Claims, No Drawings

TRICYCLIC FUSED PYRIMIDINE DERIVATIVES, THEIR PRODUCTION AND USE

BACKGROUND OF THE INVENTION

This invention relates to novel tricyclic fused pyrimidine derivatives useful as medicines Pyrazolo[3,4-d]pyrimidine derivatives having, among others, analgesic, antiinflammatory and diuretic actions are disclosed in Japanese Unexamined Patent Publication No. 31694/1978, Japanese Unexamined Patent Publication No. 5082/1986 corresponding to EP166054, and those having, among others, an action of ameliorating cerebral dysfunction are disclosed in Japanese Unexamined Patent Publication No. 10788/1988 corresponding to EP237289. While tricyclic fused pyrimidine derivatives, the fused ring formed at 2- and 3-positions of a 3-aminopyrazolo[3,4-d]pyrimidine ring, have been synthesized [cf. EP306185], tricyclic fused pyrimidine derivatives, wherein at least one of the 1 and 3-positions is hydrogen or an optionally substituted aralkyl group, are novel compounds which have not been known at all.

On the other hand, adenosine, as one of the important constituents of a living body, plays an important role for appearance, maintenance and control of various physiological functions intra- and extracellularly. More specifically, adenosine displays a variety of physiological actions in most of the organs and tissues, for example inhibition of cerebral function, vasodilation, cardiac depression, renal vasoconstriction, inhibition of platelet aggregation, modulation of insulin secretion, dysfunction of lymphocytes and modulation of renin release. These actions occur via adenosine receptors which are widespread on the surface of cells in a living body [J. W. Daly, J. Med. Chem., 25,(1982), M. Williams et al., Annu. Rep. Med. Chem., 22, 1 (1987), A. J. Bridges et al., Annu. Rep. Med. Chem., 23, 41 (1988)]. Therefore, diseases caused by physiological abnormality due to changes of interaction between adenosine and its receptors occur generally in the neurosecretion system, cardiovascular and gastro-intestinal tract system. Use of an adenosine antagonist inhibiting the interaction between adenosine and its receptors is considered useful for the therapy and prophylaxis of these diseases [M. Williams et al., Pharm. Biochem. & Behavior, 29, 433 (2988)]. Theophylline having an adenosine antagonist activity, for example, has various pharmacological activities including stimulation of the central nervous system and heart muscle, diuretic action and relaxation of smooth muscle, especially bronchial smooth muscle, and has been widely used clinically. In the cerebral tissue, it is considered that, under conditions of hypoxia or when cerebral blood circulation is blocked, adenosine triphosphate (ATP) of a high-energy compound is decreased to increase the adenosine concentration, and the adenosine acts on the adenosine receptor ($A_1$) on nerve terminals to cause decrease of intracellular cyclic AMP concentration, opening of $K^+$ channels and reduction of the $Ca^{2+}$ influx, resulting in inhibiting the release of cerebral neuro-transmitters such as acetylcholine, noradrenaline, dopamine and serotonin, thus abnormality occurring in cerebral function and metabolism [B. B. Fredholm et al., Trends in Pharm. Sci. 9, 130 (1988)].

DETAILED DESCRIPTION

The present invention provides novel tricyclic pyrimidine derivatives which are useful for the therapy and prophylaxis, by the action of ameliorating cerebral function based on a strong adenosine-antagonism, of mental disorders, neurological symptoms, etc. including symptoms of dementia, caused by cerebral apoplexy, brain injury or cerebral atrophy.

The present invention relates to a compound represented by the general formula (I)

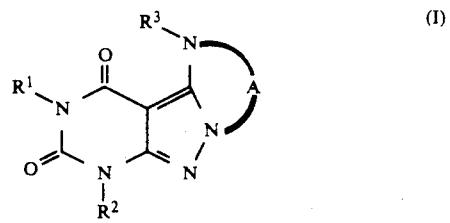

wherein either one of $R^1$ and $R^2$ stands for hydrogen or an optionally substituted aralkyl group and the other stands for hydrogen, an optionally substituted aralkyl group or an aliphatic hydrocarbon group; $R^3$ stands for hydrogen, an aliphatic hydrocarbon group or acyl group; and A stands for an optionally substituted divalent hydrocarbon chain having 2 to 4 carbon atoms or a salt thereof.

Referring to the above-mentioned general formula (I), as the optionally substituted aralkyl group shown by $R^1$ or $R^2$, mention is made of an alkylene group having 1 to about 4 carbon atoms (e.g. methylene, ethylene, trimethylene, tetramethylene, etc.) combined with an aromatic hydrocarbon group (e.g. phenyl, naphthyl, etc.), and the aromatic hydrocarbon group may be substituted with 1 to 3 substituents such as halogen (e.g. fluorine, chlorine, bromine), a lower($C_{1-4}$) alkyl (e.g. methyl, ethyl), a lower($C_{1-4}$) alkoxy (e.g. methoxy, ethoxy), nitro, amino, N-lower($C_{1-4}$) alkylamino (e.g. methylamino), N,N-dilower ($C_{1-4}$) alkylamino (e.g. dimethylamino), hydroxy, trifluoromethyl, carbamoyl, N-lower($C_{1-4}$) alkylcarbamoyl (e.g. N-methylcarbamoyl), N,N-dilower($C_{1-4}$) alkylcarbamoyl (e.g. N,N-dimethylcarbamoyl), etc. Among these substituents, halogen, lower alkyl, lower alkoxy, nitro, amino, etc. are preferable, more preferably halogen. The substitution position is not specifically limited, and it may be any of ortho-, meta- and para-positions. When the substituent is halogen, the meta-position is preferable. As the aliphatic hydrocarbon group shown by $R^1$ or $R^2$, use is made of, for example, an alkyl group having 1 to about 8 carbon atoms (e.g. methyl, ethyl, propyl, i-propyl, butyl, i-butyl, pentyl, i-pentyl, hexyl, heptyl, octyl, etc.), an alkenyl group having about 2 to about 8 carbon atoms (e.g. vinyl, allyl, 1-propenyl, isopropenyl, 2-butenyl, 1,3-butadienyl, 2-pentenyl, 1-hexenyl, 1-heptenyl, 1-octenyl, etc.), etc. Among them, aliphatic hydrocarbon groups having about 2 to about 5 carbon atoms are preferable, especially alkyl groups having about 2 to about 5 carbon atoms are preferable.

Among the compounds represented by the above-mentioned general formula (I), compounds wherein either one of $R^1$ and $R^2$ stands for an optionally substituted aralkyl group and the other stands for an optionally substituted aralkyl group or an aliphatic hydrocarbon group are preferable, especially compounds wherein $R^1$ is an aliphatic hydrocarbon group and $R^2$ is an optionally substituted aralkyl group are preferable.

As the aliphatic hydrocarbon group shown by $R^3$, mention is made of, for example, an alkyl group having 1 to about 3 carbon atoms (e.g. methyl, ethyl, propyl, i-propyl), an alkenyl group having about 2 to about 3 carbon atoms (e.g. vinyl, allyl,1-propenyl, isopropenyl), and ,among them, alkyl groups having 1 to about 3 carbon atoms are preferable.

As the acyl group shown by $R^3$, mention is made of that derived from an organic acid, for example, alkanoyl groups preferably having not more than 7 carbon atoms (e.g. acetyl, trifluoroacetyl, propionyl, butyryl, valeryl, cyclohexanecarbonyl, etc.), aromatic carbonyl group (e.g optionally substituted benzoyl, etc.), alkoxycarbonyl groups preferably those whose carbon number of the alkyl moiety is 1 to about 4 (e.g. methoxycarbonyl, ethoxycarbonyl, propoxycarbonyl, etc.), carbamoyl, formyl, etc. Among them, alkanoyl groups whose carbon number is not more than 7 or alkoxycarbonyl groups whose carbon number at the alkyl moiety is 1 to about 4 are preferable, especially acetyl, propionyl and methoxycarbonyl are preferable. As the divalent hydrocarbon chain having 2 to 4 carbon atoms shown by A, mention is made of $C_{2-4}$ alkylene (e.g. ethylene, trimehtylene, tetramethylene), $C_{2-4}$ alkenylene (e.g. vinylene, propenylene, etc.), etc.

The hydrocarbon chain may have a substituent, and, as the substituent, mention is made of, for example, an optionally substituted aliphatic hydrocarbon group (e.g. aliphatic hydrocarbon group which may be substituted with an optionally substituted amino (e.g. amino, dimethyl amino, cyclic amino), nitro, hydroxy, alkoxy having 1 to about 4 carbon atoms, alkylthio having 1 to about 4 carbon atoms), among them, an alkyl group having 1 to about 8 carbon atoms (e.g. methyl, ethyl, propyl, isopropyl, cyclopropyl, butyl, isobutyl, pentyl, isopentyl, hexyl, isohexyl, heptyl, octyl, etc.), an optionally substituted aromatic hydrocarbon group (e.g. phenyl optionally substituted at ortho-, meta- or para-position, with 1 to 2 substituents such as an optionally substituted amino, nitro, hydroxy, methoxy, methyl, phenyl, etc., etc.), halogen (e.g. F, Cl, Br, etc.), nitro, amino, oxo, etc., and the neighboring two substituents may be combined with each other to form a cyclic group (e.g. cyclic aliphatic hydrocarbon groups having about 5 to about 8 carbon atoms, etc.).

As the above-mentioned optionally substituted divalent hydrocarbon chain having about 2 to about 4 carbon atoms shown by A, mention is made of, preferably, alkylene having 2 to 4 carbon atoms or hydrocarbon chain represented by the formula:

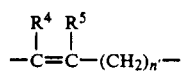

wherein $R^4$ and $R^5$ each stand for hydrogen, an optionally substituted aliphatic hydrocarbon group, an optionally substituted aromatic hydrocarbon group or halogen, or $R^4$ and $R^5$ may be combined to form a cyclic aliphatic hydrocarbon group having about 5 to about 8 carbon atoms represented by the formula:

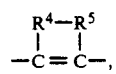

and n' denotes an integer of 0 to 2; A can also represent a hydrocarbon chain represented by the formula:

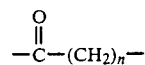

wherein n denotes an integer of 1 to 3, and, among them, ethylene and a group represented by the formula:

wherein $R^4$ and $R^5$ each stand for hydrogen, phenyl which may have a substituent such as halogen, lower ($C_{1-4}$) alkoxy, etc. or alkyl having 1 to about 4 carbon atoms which may have a substituents such as an optionally substituted amino (e.g. dimethylamino, etc.) are preferable.

Among the compounds [Compound (I)] represented by the above-mentioned formula (I), compounds (I) wherein $R^1$ stands for an aliphatic hydrocarbon group having 2 to 5 carbon atoms (especially an alkyl group having 3 to 5 carbon atoms), $R^2$ stands for hydrogen or an optionally substituted phenyl- lower ($C_{1-4}$) alkyl group(especially benzyl group which may be substituted with halogen), $R^3$ stands for hydrogen, methyl, acetyl or methoxycarbonyl (especially hydrogen), and A stands for ethylene or a hydrocarbon chain represented by the formula:

wherein $R^4$ and $R^5$ each stand for hydrogen, a $C_{1-8}$ lower alkyl group or an optionally substituted aromatic hydrocarbon group (especially hydrogen, $C_{1-4}$ alkyl, phenyl which may be substituted with lower ($C_{1-4}$) alkoxy) are further preferable.

Examples of the salts of compound (I) include pharmacologically acceptable ones, i.e. acid addition salts such as inorganic acid salts e.g. hydrochloride, hydrobromide, sulfate, nitrate, phosphate, etc., organic acid salts such as acetate, tartrate, citrate, fumarate, maleate, etc.

PRODUCTION METHOD

The above-mentioned compounds of the general formula (I) can be produced by, for example, methods shown below.

Process (a)

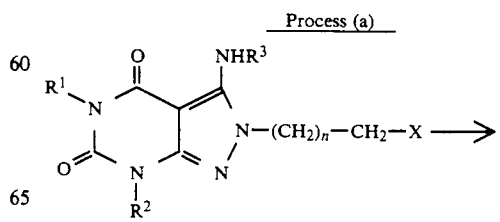

II

-continued

Process (a)

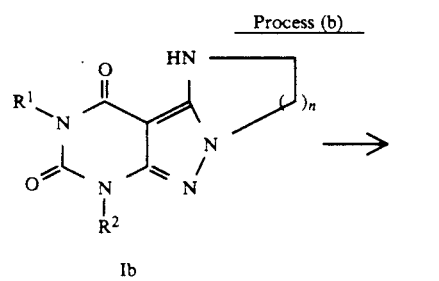

Ia

Process (d)

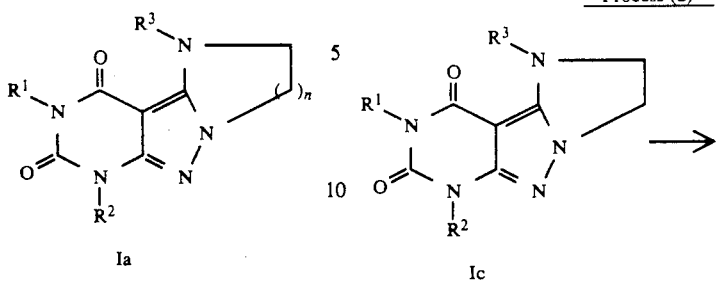

Ic wherein $R^1$, $R^2$ and $R^3$ are of the same meaning as defined above, X stands for halogen, and n denotes an integer of 1 to 3.

Process (b)

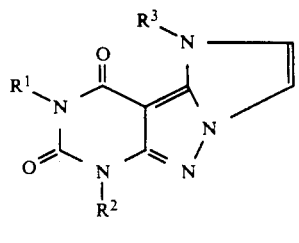

Ib

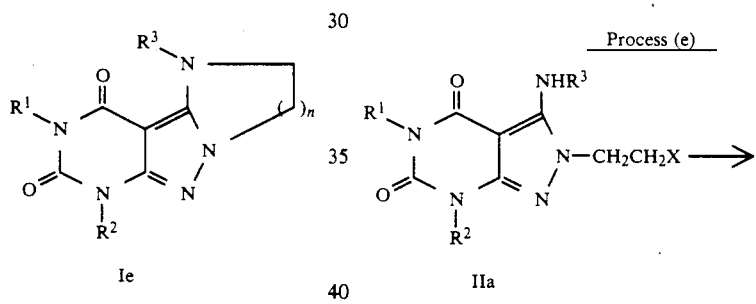

If wherein $R^1$, $R^2$ and $R^3$ are of the same meaning as defined above.

Ie

Process (e)

IIa wherein $R^1$, $R^2$, $R^3$ and n are of the same meaning as defined above, provided that $R^3$ is not hydrogen.

Process (c)

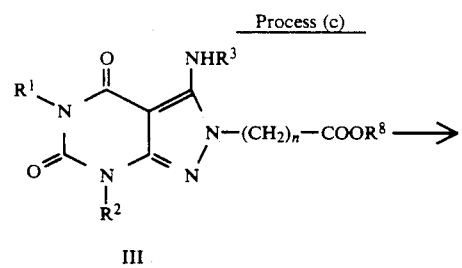

III

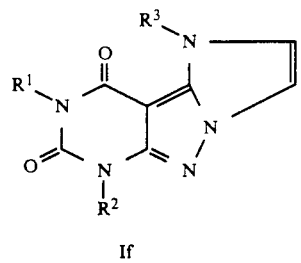

If wherein $R^1$, $R^2$, $R^3$ and X are of the same meaning as defined above.

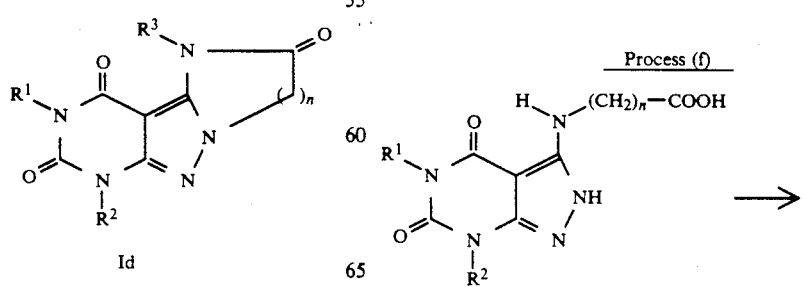

Id

Process (f)

XVI wherein $R^1$, $R^2$, $R^3$ and n are of the same meaning as defined above, and $R^6$ stands for a lower alkyl group.

-continued

Process (f)

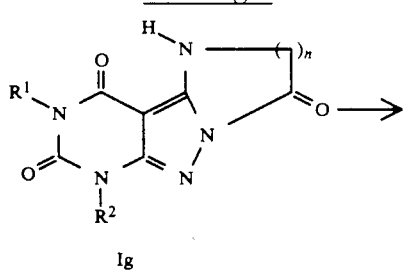
Ig

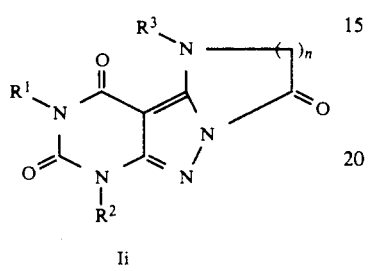
Ih

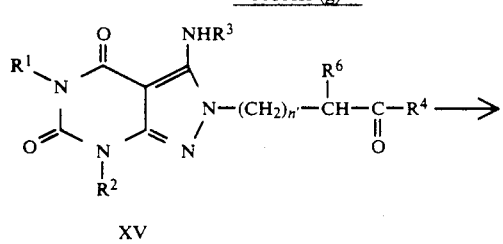
Ii wherein $R^1$, $R^2$, $R^3$ and n are of the same meaning as defined above, provided that $R^3$ is not hydrogen.

Process (g)

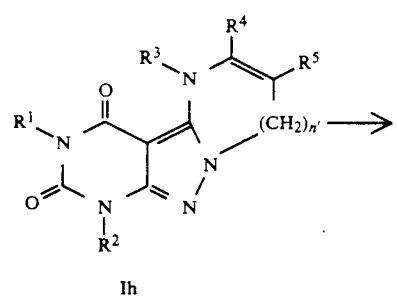
XV

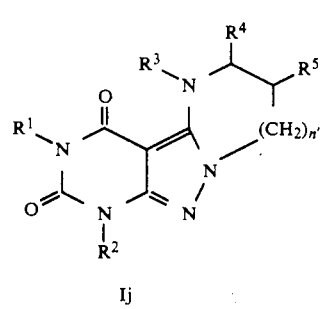
Ij wherein $R^1$, $R^2$, $R^3$, $R^4$, $R^5$ and X are of the same meaning as defined above, and n' denotes an integer of 0 to 2.

Process (h)

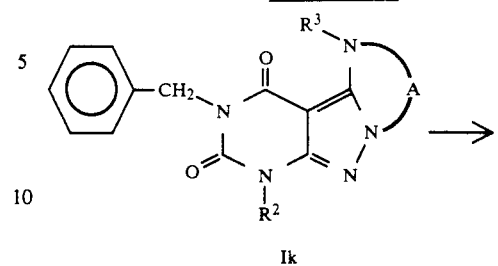
Ik

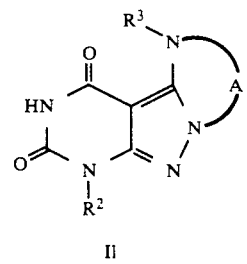
Il wherein $R^2$, $R^3$ and A are of the same meaning as defined above, provided that $R^2$ is not an optionally substituted benzyl group.

Process (i)

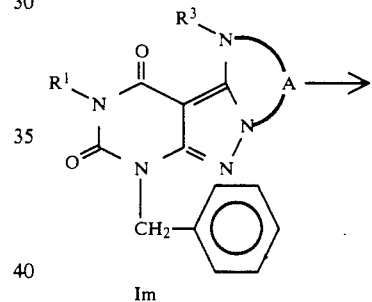
Im

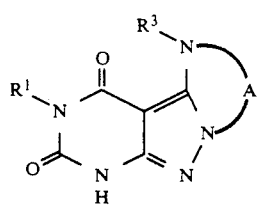
In wherein $R^1$, $R^3$ and A are of the same meaning as defined above, provided that $R^1$ is not an optionally substituted benzyl group.

Process (j)

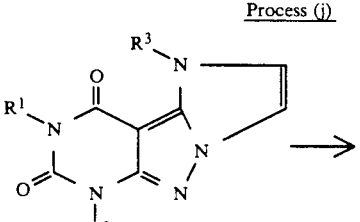
If

-continued

Process (j)

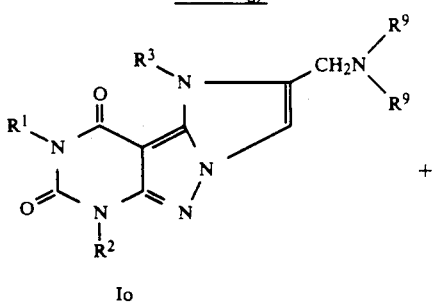

Io

+

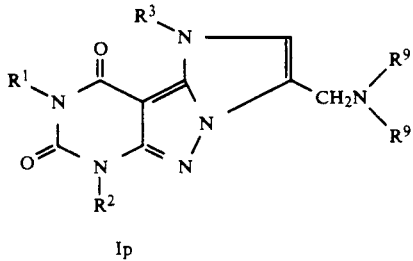

Ip wherein $R^1$, $R^2$ and $R^3$ are of the same meaning as defined above, and $R^9$ is a lower alkyl group or

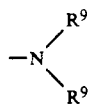

is a cyclic amino group.

The above-mentioned process (a) is a ring-closure reaction in the presence of a base, and the amount of the base is in the range of 1 to about 3 mol. relative to 1 mol. of compound (II). As the base, use is made of, among others, sodium hydride, potassium t-butoxide, potassium carbonate and sodium carbonate. As the solvent, use is made of a polar aprotic solvent such as dimethylformamide, dimethylacetamide, dimethyl sulfoxide, acetonitrile, etc. The reaction is carried out preferably under ice-cooling or at temperatures not higher than about 100° C. for about 0.5 to about 30 hours. When a strong base such as sodium hydride or potassium t-butoxide is employed, the reaction is carried out preferably by dissolving compound (II) in a solvent and then adding portionwise such a base as above to the solution under ice-cooling. The reaction can be conducted advantageously by suspending a strong base such as sodium hydride in a solvent such as dimethylformamide and then adding to the suspension portionwise under ice-cooling a solution of compound (II) in the same solvent. After the addition of a base in such a manner as above, the reaction is preferably conducted by raising the reaction temperature to about room temperature and allowing the reaction to proceed for further 1 to 2 hours. On the other hand, when the reaction is conducted in the presence of a weak base such as potassium carbonate or sodium carbonate, it is preferable to allow the compound (II) to react with such a base as mentioned above in a solvent such as dimethylformamide (DMF) at about 50° C. to about 130° C. for about 10 hours to about 30 hours. After completion of the reaction, the solvent is distilled off, then the residue is poured into ice-water, and resulting crystals are recrystallized from e.g. aqueous alcohol, thereby the desired reaction product can be easily obtained. Depending on cases, a conventional isolation and purification step such as column chromatography can be resorted to.

The process (b) is to obtain compound (Ie) by subjecting compound (Ib) to alkylation or acylation. As an alkylation agent, mention is made of an alkyl halogenide (e.g. methyl iodide, ethyl iodide, propyl idodide, benzyl bromide, etc.), and, as an acylating agent, mention is made of an acid anhydride (e.g. acetic anhydride, propionic anhydride, butyric anhydride, etc.) or an acid halogenide (e.g. acetyl chloride, propionyl chloride, butyryl chloride, etc.). And, when alkoxycarbonylation is conducted, use is made of an alkyl halogenocarbonate (e.g. methyl ester of chlorocarbonic acid, ethyl ester of chlorocarbonic acid, etc.). These reagents are used in an excess amount of about 1 to about 5 mol. relative to 1 mol. of the compound (Ib), and the reaction is allowed to proceed in the presence of a suitable base. As the base, use is made of potassium carbonate, sodium carbonate, triethylamine, pyridine, etc., and, depending on cases, the reaction is conducted by the addition of a catalytic amount of dimethyl aminopyridine. As the solvent, use is made of pyridine, dimethylformamide, dimethylacetamide, acetonitrile, dioxane, etc., and the reaction is allowed to proceed preferably under ice-cooling or at temperatures not higher than about 100° C. for about 1 to about 50 hours. The alkylation is conducted preferably using about 1 to about 2 mol. of an alkyl halogenide in dimethylformamide at temperatures ranging from room temperature to about 50° C. for about 5 to about 20 hours. And the acylation is conducted preferably using about 1 to about 3 mol. of an acid anhydride in pyridine at temperatures ranging from about 50° C. to about 100° C. for about 5 to about 20 hours. Depending on cases, the reaction can be conducted more advantageously by adding a catalytic amount of dimethylaminopyridine.

The alkoxy carbonylation is desirably carried out in a solvent such as dioxane, etc. in the presence of a base such as triethylamine by adding alkyl halogenocarbonate under ice cooling or at temperatures up to room temperatures, then the reaction being allowed to proceed at temperatures ranging from temperatures to about 60° C. for about 5 to about 20 hours. The reaction product can be isolated as crystals easily by evaporating the reaction solvent, and then by pouring the residue into ice-water, or by employing a conventional isolation and purification means.

The process (c) is a lactam-ring formation reaction in the presence of a base in an amount of 1 to about 3 mol. relative to 1 mol. of compound (III). As preferable bases, there may be used sodium methoxide, sodium ethoxide, etc. As preferable solvents, there may be used alcohol solvents such as methanol, ethanol, etc. The reaction is conducted preferably under icecooling or temperatures not higher than about 50° C. for about 30 minutes to about 2 hours. After completion of the reaction, the solvent is distilled off, and the residue is dissolved in water, followed by neutralization with about 1N to about 2N hydrochloric acid to obtain the desired product as crystals.

The process (d) is to obtain compound (If) by dehydrogenation, and the reaction is carried out in a conventional organic solvent such as dimethylformamide, dimethylacetamide, acetonitrile, dioxane, toluene, benzene, chloroform, methylene chloride, etc. at temperatures ranging from about 50° C. to about 150° C. for a period ranging from about 5 hours to about 60 hours.

The reaction can also be conducted in the presence of benzoyl peroxide, 2,3-dichloro-5,6-dicyano-1,4-benzoquinone (DDQ), selenium dioxide, manganese dioxide, etc., or in the presence of of a base such as potassium carbonate or sodium carbonate, and it is especially preferable to conduct the reaction, using, as an oxidant, about 1 to about 2 mol. of benzoyl peroxide, in an aprotic solvent such as chloroform by heating under reflux for about 5 to about 15 hours.

The process (e) is to obtain the compound (If) from compound (IIa) directly. The reaction conditions are analogous to those in the case of process (a). In the case of process (e), as the base, use is made of potassium carbonate or sodium carbonate, and the reaction is preferably conducted in a solvent such as dimethylformamide, dimethylacetamide, etc. The reaction is conducted more preferably at temperatures ranging from about 80° C. to about 120° C. for about 20 to about 40 hours. The products obtained by process (d) and process (e) can be isolated as crystals easily by, after distilling off the reaction solvent, pouring the residue into water, or by subjecting the residue to conventional isolation and purification means such as column chromatography, etc.

The process (f) is to obtain the compound (Ii) by subjecting the compound (XVI) to a ring-closure reaction in the presence of a dehydrating agent to give compound (Ig), then by subjecting, when desired, to acylation or alkylation like in the case of process (b) to give compound (Ii). As the dehydrating agent employable for the reaction from compound (XVI) to compound (Ig), use is made of dicyclohexyl carbodiimide (DCC), carbonyl diimidazole (CDI), etc. or a chlorinating agent such as thionyl chloride, phosphorus oxychloride, etc. It is preferable to use about 1 to about 10 equivalents of a dehydrating agent relative to the compound (XVI) in such a solvent as methylene chloride, chloroform, benzene, etc. and to allow the reaction to proceed at temperatures ranging from room temperature to about 100° C. for about 1 to about 10 hours. It is especially preferable to conduct the reaction in a solvent such as chloroform or methylene chloride, using about 5 to about 10 equivalents of thionyl chloride, for about 1 to about 5 hours by heating under reflux.

The process (g) comprises dehydration of compound (XV) under acid or basic conditions to give the desired compound (Ih), and, when desired, subjecting the compound (Ih) to reduction to yield compound (Ij). In the reaction of compound (XV) to compound (Ih), as an acid, use is made of an organic or inorganic acid such as p-toluenesulfonic acid, hydrochloric acid, sulfuric acid, etc., and, as a base, use is made of triethylamine, potassium carbonate, sodium carbonate, sodium hydroxide, etc. in an amount ranging from a catalytic amount to about 2 equivalents relative to the compound (XV), and, as a solvent, use is made of benzene, toluene, xylene, methyl ethyl ketone, etc., and the reaction is allowed to proceed at temperatures ranging from room temperature to about 150° C. for about 5 hours to about 3 days. Especially, it is preferable to conduct the reaction in a solvent such as benzene or toluene, etc., using a catalytic amount of ptoluenesulfonic acid, by heating under reflux for about 10 to about 20 hours. The hydrogenation of compound (Ih) to compound (Ij) is carried out preferably in a conventional organic solvent such as methanol, ethanol, chloroform, dichloromethane, benzene, acetic acid, etc., in hydrogen streams of normal to about 5 atmospheric pressure in the presence of a suitable catalyst, at temperatures ranging from room temperature to about 50° C. for about 1 to about 10 hours. As the catalyst, Raney nickel, palladium-carbon, platinumcarbon, platinum oxide or rhodium catalyst, etc. are exemplified.

The products obtained by process (f) and process (g) can be isolated easily as crystals, after distilling off the reaction solvent, by a conventional isolation and purification means.

The process (h) is to obtain compound (Il) by subjecting compound (Ik) to debenzylation, and the process (i) is to obtain compound (In) by subjecting compound (Im) to debenzylation..

The process (j) is to obtain the compounds (Io) and (Ip) by subjecting the compound (If) to aminomethylation by a Mannich reaction.

The reaction is conducted using about 2 to about 5 mol. of paraformaldehyde and amine relative to 1 mol. of the compound (If). As the amine, use is made of ammonia, primary amine, secondary amine, etc. Usually, secondary amine (e.g. dimethylamine, morpholine, etc.) is employed. Amines can also be used as salts thereof (e.g. hydrochloride, acetate, etc.) in the reaction. As the solvent, use is made of a protic solvent such as acetic acid, alcohols (e.g. methanol, ethanol, etc.) and mixtures thereof can also be used. The reaction condition varies with an amine or a solvent. It is preferable to carry out the reaction at temperatures ranging from room temperatures to about 100° C. for 1 to about 10 hours. More preferably, the reaction is carried out in acetic acid in the presence of paraformaldehyde and an aqueous solution of dimethylamine at temperatures ranging from about 50° C. to about 80° C. for 1 to about 3 hours. When the compound (If) is used, the product is obtained as a mixture of compounds substituted at the 6- and 7positions (Io and Ip), which can easily be obtained as respective crystals by a conventional isolation and purification means (recrystallization or silica gel column chromatography).

Among these compounds, the starting compounds (II), (III), (XV) and (XVI) are novel ones, which can be synthesized by the following methods. Starting with compounds (IV) and (XI) synthesized by a method analogous to that described in Chem. Ber., 95, 1597 (1962) and Ann. Chem., 691, 142 (1966), the compound (II) can be obtained by methods described in Chem. Pharm. Bull., 27, 1328 (1978) and Chem. Pharm. Bull., 27, 1965 (1978) or in Japanese Unexamined Patent Publication No. 31694/1978, Japanese Unexamined Patent Publication No. 5082/1986 corresponding to EP 166054. More specifically, the 3-amino derivative (IX) obtained by four processes shown by the process (k), (1), (m) or (n) is allowed to react with one of the various alkyl dihalides (e.g. 1-bromo-2-chloroethane, 1-bromo-3-chloropropane, 1-bromo-4-chlorobutane, etc.) as shown by process (o) in an aprotic solvent such as dimethylformamide, etc. in the presence of potassium carbonate, sodium carbonate, etc. at temperatures ranging from 50° C. to 120° C. for about 10 to about 20 hours to obtain the starting compound (II). On the other hand, the starting compound (III) can be obtained, as shown by process (p), by allowing compound (IX) to react with a halogenated aliphatic alkyl ester (e.g. bromoacetic acid methyl ester, bromoacetic ethyl ester, etc.), in the presence of potassium carbonate or sodium carbonate, in an aprotic solvent such as dimethylformamide, etc. at temperatures ranging from room temperature to about 80° C. for about 1 to about 5 hours.

The starting compound (XVI) can be obtained by subjecting the compound (VIIIb) prepared by the method shown in process (1) to alkaline hydrolysis as shown in process (r).

The starting compound (XV) can be prepared, as shown in process (q), by allowing the above-mentioned 3-amino derivatives (IX) to react with a haloketone (e.g. bromoacetone, chloroacetone, 3-chloro-2-butanone, phenacyl chloride, phenacyl bromide, 2chlorocyclohexanone, 1-chlorohexane-2-one, etc.) in the presence of a base such as potassium carbonate, sodium carbonate, triethylamine, etc., and in the presence of potassium iodide as a reaction promoter, at temperatures ranging from room temperature to about 50° C. for about 1 to about 4 days.

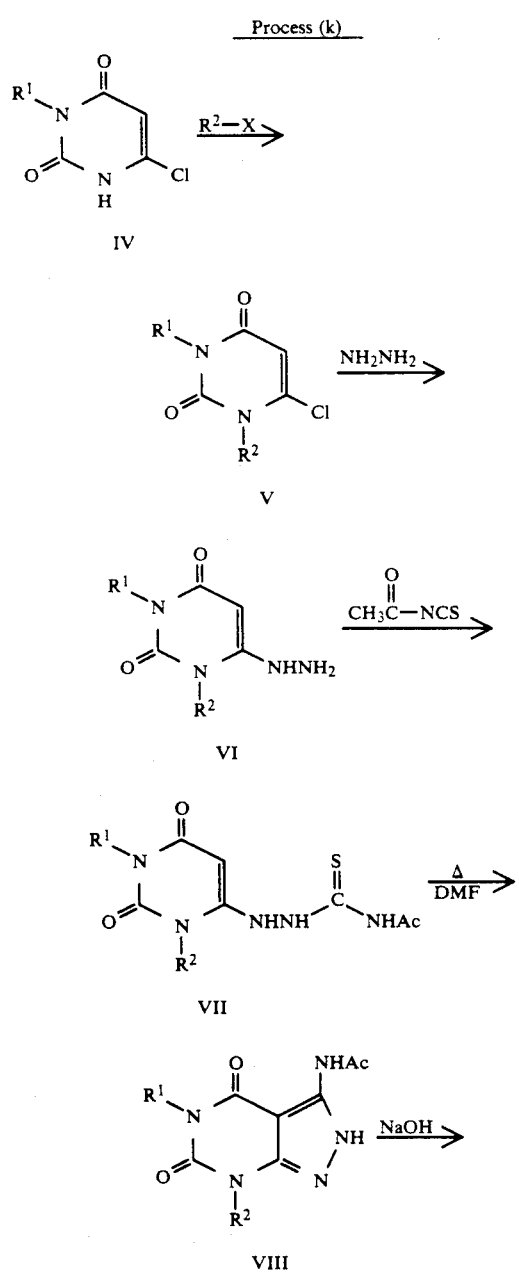

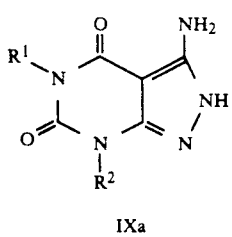

wherein $R^1$, $R^2$ and X are of the same meaning as defined above.

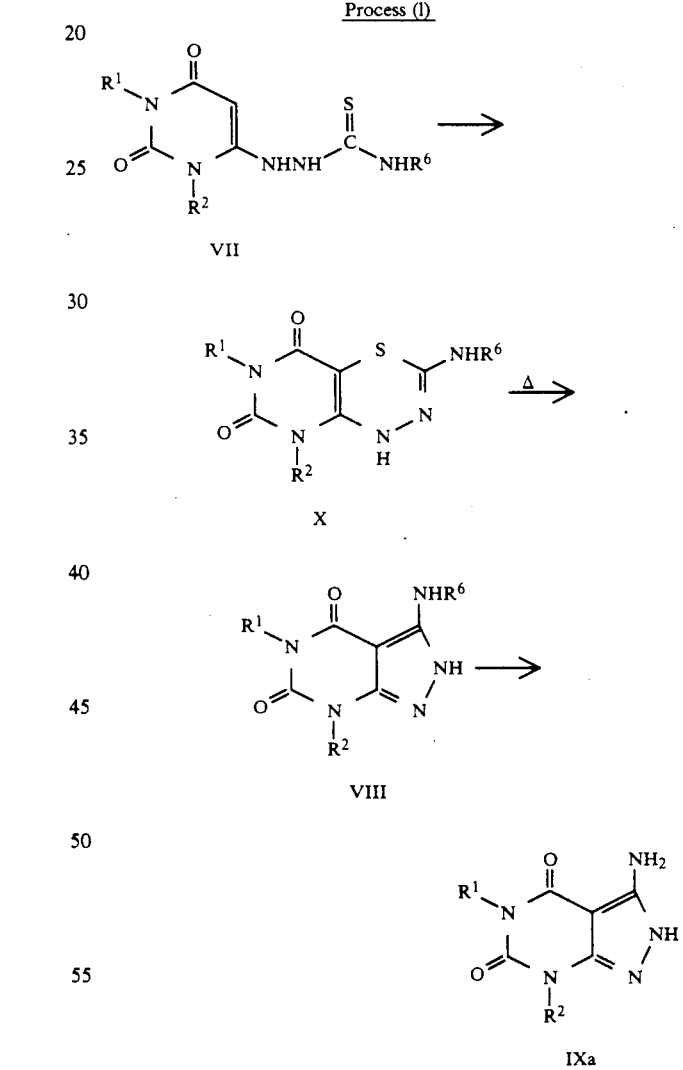

wherein $R^1$ and $R^2$ are of the same meaning as defined above; $R^6$ stands for a lower alkyl, acyl group (acetyl, benzoyl, etc.) or a group represented by the formula:—$(CH_2)_nCOOR^7$ (wherein n is of the same meaning as defined above, and $R^7$ stands for a lower alkyl group).

Process (m)

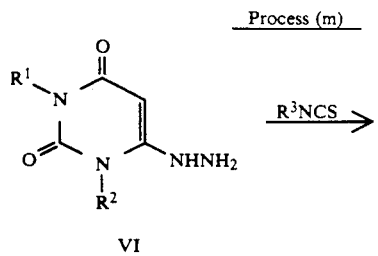

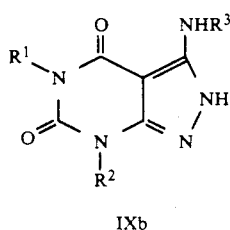

wherein $R^1$, $R^2$ and $R^3$ are of the same meaning as defined above, provided that $R^3$ is not hydrogen.

Process (n)

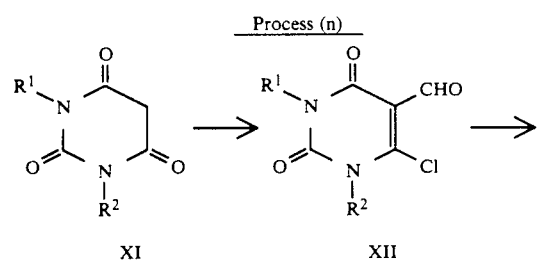

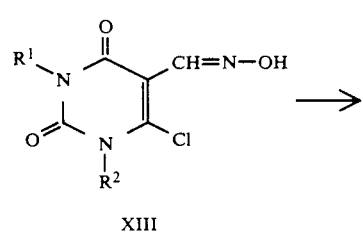

wherein $R^1$ and $R^2$ are of the same meaning as defined above, provided that $R^1 = R^2$.

Process (o)

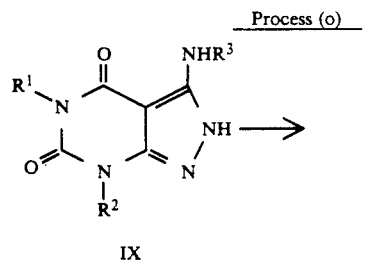

-continued
Process (o)

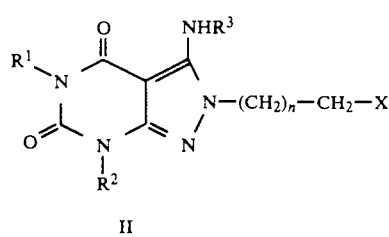

wherein $R^1$, $R^2$, $R^3$, X and n are of the same meaning as defined above.

Process (p)

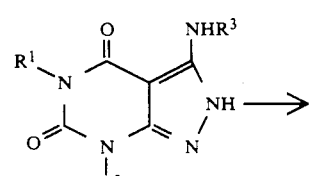

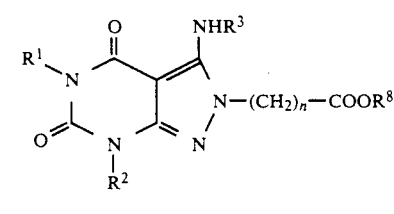

wherein $R^1$, $R^2$, $R^3$, $R^8$ and n are of the same meaning as defined anove.

Process (q)

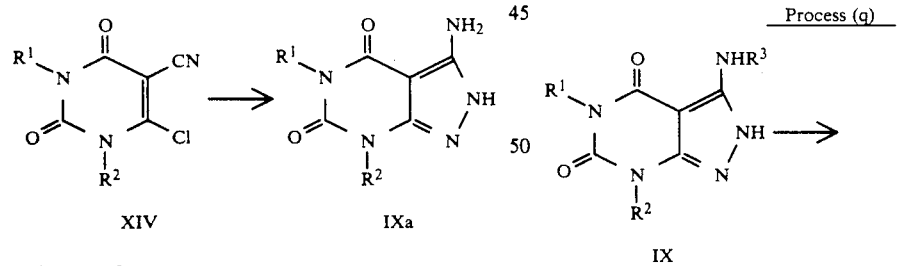

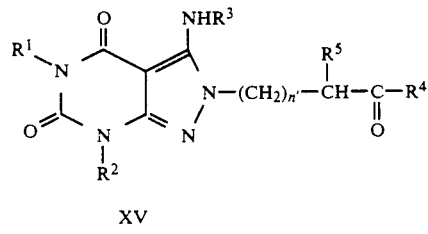

wherein $R^1$, $R^2$, $R^3$, $R^4$, $R^5$ and n' are of the same meaning as defined above.

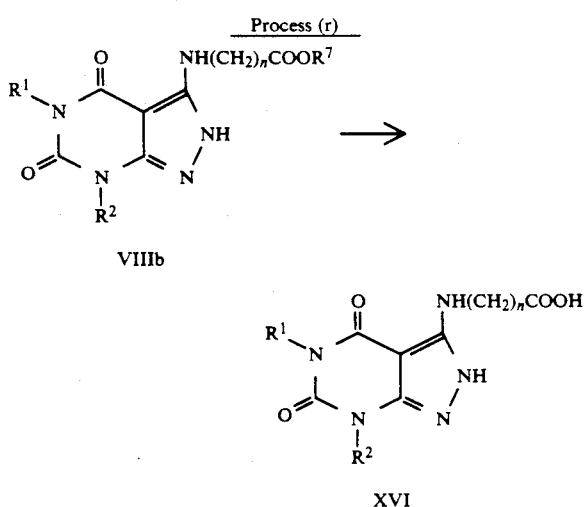

wherein $R^1$, $R^2$, $R^7$ and n are of the same meaning as defined above.

Action

The compounds (I) of the present invention have a strong antagonistic action in the adenosine-receptor derived from rat cerebral cortex, cause acceleration of release of various neurotransmitters in the brain and increase of the concentration thereof in the brain to perform activation of cerebral functions and metabolisms. The compounds (I) are useful owing to their properties of activating cerebral functions and metabolisms which are decreased by the occurrence of cerebrovascular disease, brain injury or aging, for the therapy and prophylaxis in mammals, of neurological or psychic changes (neurological deficits or psychic disturbances) including dementia symptoms caused by cerebral apoplexy, brain injury or cerebral atrophy (Alzheimer's diseases, etc.), and they can be used for the prophylaxis and therapy of, for example, memory impairment (e.g. amnesia, retention disturbance, etc.), disorientation for place and time, emotional disturbances, decreased spontaneity and dystropy. Also, the compounds (I) are of low toxicity [$LD_{50}$(p.o.): not less than 1000 mg/kg body weight (mouse)]. When the compounds (I) are used as medicines mentioned above, they can be safely administered to mammals including man orally or non-orally as such or an admixture with suitable, pharmaceutically acceptable carriers, excipients or diluents in such dosage forms as powder, granules, tablets, capsules, injections, suppositories, ointments and so forth.

Additives employable for such medicinal preparations as mentioned above include excipients e.g. sucrose, lactose, glucose, starch, mannitol, sorbitol, micro-crystalline cellulose, talc, cryclodextrin, etc., binders e.g. hydroxypropylcellulose, hydroxypropyl methylcellulose, carboxymethylcellulose, pullulan, methylcellulose, polyvinylpyrrolidone, gelatin, gum arabic, polyethylene glycol, sucrose, starch, etc., disintegrants e.g. starch, carboxymethylcellulose, calcium salt of carboxymethylcellulose, hydroxypropylcellulose of low substitution degree, etc., lubricants e.g. talc, magnesium stearate, etc., coloring agents e.g. hydroxypropylmethylcellulose, ethylcellulose, hydroxymethylcellulose, hydroxypropylmethylcellulose phthalate, Eudragit [Rohm Pharma GmbH (W. Germany); methacrylic acid.acrylic acid copolymer], titanium oxide, red iron oxide, etc., preservatives e.g. sodium benzoate, sodium hydrogensulfite, etc., suspending agents e.g. methyl cellulose, aluminum stearate, etc., dispersants e.g. Polysorbate 80, Emal Gel 408, Emasol 310, etc. solvents e.g. water, base materials e.g. cacao butter, polyethylene glycol, Wittepsol, white petrolatum, etc., and these adjuvants may be suitably selected in accordance with the types of preparations.

Although the dosage should vary with such factors as the subject diseases, symptoms, subject patients, the routes of administration, etc., when orally administered to an adult human patient with dementia symptoms caused by cerebral apoplexy, brain injury or cerebral atrophy, preferable dosage is in the range of from about 1 to about 50 mg/kg (body weight) 1 to about 3 times a day, more preferably about 1 to about 20 mg/kg (body weight) 1 to about 3 times a day.

Working Examples

The following reference examples, working examples, formulation examples and experimental examples are intended to illustrate the present invention in further detail and should by no means be construed as limiting the scope of the present invention.

Abbreviations employed in the present specification are exemplified below.

| | |
|---|---|
| Me: methyl | Hex: hexyl |
| Et: ethyl | Hep: heptyl |
| Pr: propyl | All: allyl |
| Bu: butyl | Ac: acetyl |
| Pen: pentyl | Ph: phenyl |
| s: singlet   d: doublet   t: triplet | br s: broad singlet |
| m: multiplet | |

REFERENCE EXAMPLE 1

6-(4-Acetylthiosemicarbazido)-1-benzyl-3-propyl-pyrimidine-2,4(1H,3H)-dione

Acetyl chloride (11 g) was added to a suspension of potassium thiocyanate (20 g) in dioxane (300 ml) and the mixture was stirred for 5 hours at room temperature. After removal of an insoluble material by filtration, the filtrate was stirred at room temperature and 1-benzyl-6-hydrazino-3-propylpyrimidine-2,4(1H,3H)-dione (18.2 g) was added in portions to the filtrate at room temperature. The reaction mixture was allowed to stir for one hour at room temperature and was concentrated to dryness. The resulting product was triturated with isopropyl ether to give crystals (24 g, 96%), m.p. 184° to 185° C.

Elemental Analysis for $C_{17}H_{21}N_5O_3S$: Calcd.(%): C, 54.38; H, 5.64; N, 18.65, Found (%): C, 54.21; H, 5.87; N, 18.59.

The following compounds (Reference Examples 2 to 5) were synthesized by the same procedure.

REFERENCE EXAMPLE 2

6-(4-acetylthiosemicarbazido)-1-(4-chlorobenzyl)-3-propylpyrimidine-2,4(1H,3H)-dione, m.p. 195°–196° C.

REFERENCE EXAMPLE 3

6-(4-Acetylthiosemicarbazido)-1-(3-chlorobenzyl)-3-propylpyrimidine-2,4(1H,3H)-dione, m.p. 189°–190° C.

REFERENCE EXAMPLE 4

6-(4-Acetylthiosemicarbazido)-1-(2-chlorobenzyl)-3-propylpyrimidine-2,4(1H,3H)-dione, m.p. 126°–127° C.

REFERENCE EXAMPLE 5

6-(4-Acetylthiosemicarbazide)-3-benzyl-1-butylpyrimidine-2,4(1H,3H)-dione, m.p. 124°–125° C.

REFERENCE EXAMPLE 6

3-Acetylamino-8-benzyl-6-propyl-1H-pyrimido[4,5-e][1,3,4]thiadiazine-5,7(6H,8H)-dione 6-(4-Acetylthiosemicarbazido)-1-benzyl-3-propyl-pyrimidine-2,4(1H,3H)-dione (7 g) was added in portions to a mixture of N-chlorosuccinimide (3 g) at room temperature and the reaction mixture was stirred 3 further hours and then there was added hexane (200 ml). Resulting crystals were collected by filtration and washed with water to give yellowish brown crystals (9.3 g), m.p. 135°–140° C. This product was used for the subsequent reaction without further purification. In a manner analogous to the above, the following compounds (Reference Examples 7 to 10) were synthesized.

REFERENCE EXAMPLE 7

3-Acetylamino-8-(4-chlorobenzyl)-6-propyl-1H-pyrimido[4,5-e][1,3,4]thiadiazine-5,7(6H,8H)-dione, m.p. 137°–139° C.

REFERENCE EXAMPLE 8

3-Acetylamino-8-(3-chlorobenzyl)-6-propyl-1H-pyrimido[4,5-e][1,3,4]thiadiazine-5,7(6H,8H)-dione, m.p. 135°–140° C.

REFERENCE EXAMPLE 9

3-Acetylamino-8-(2-chlorobenzyl)-6-propyl-1H-pyrimido[4,5-e][1,3,4]thiadiazine-5,7(6H,8H)-dione, m.p. 135°–136° C.

REFERENCE EXAMPLE 10

3-Acetylamino-6-benzyl-8-butyl-1H-pyrimido[4,5-e][1,3,4]thiadiazine-5,7(6H,8H)dione, m.p. 136°–137° C.

REFERENCE EXAMPLE 11

3-Acetylamino-7-benzyl-5-propylpyrazolo[3,4-d]pyrimidine-4,6(5H,7H)-dione

A solution of 3-acetylamino-8-benzyl-6-propyl-pyrimido[4,5-e][1,3,4]thiadiazine-5,7(6H,8H)dione (4.0 g) in dioxane (50 ml) was refluxed for one hour. The reaction mixture was concentrated to dryness, and the concentrate was dissolved in methanol. Insoluble sulfur was filtered off. To the filtrate was added a small volume of water, which was left standing for cooling, then colorless crystals (3.4 g), m.p. 108°–110° C., were obtained.

Elemental Analysis for $C_{17}H_{19}N_5O_3$:

|  | C (%) | H (%) | N (%) |
|---|---|---|---|
| Calcd.: | 59.81; | 5.61; | 20.52, |
| Found: | 59.73; | 5.68; | 20.59. |

By a manner analogous to REFERENCE EXAMPLE 11, the following compound was synthesized.

REFERENCE EXAMPLE 12

3-Acetylamino-7-(m-chlorobenzyl)-5-propyl-pyrazolo[3,4-d]yrimidine-4,6(5H,7H)-dione, m.p. 204°–205° C.

REFERENCE EXAMPLE 13

3-Acetylamino-7-benzyl-5-propylpyrazolo[3,4-d]pyrimidine-4,6(5H,7H)-dione

A solution of 6-(4-acetylthiosemicarbazido)-1-benzyl-3-propylpyrimidine-2,4(1H,3H)-dione (3.0 g) in dimethylformamide (50 ml) was heated at 100° to 110° C. for 60 hours. The reaction mixture was concentrated and dissolved in 90% methanol. The solution was left standing for cooling to give pale brown crystals, followed by recrystallization from ethanol to obtain colorless crystals, m.p. 108° to 110° C.

|  | C (%) | H (%) | N (%) |
|---|---|---|---|
| Calcd.: | 59.81; | 5.61; | 20.52 |
| Found: | 59.64; | 5.75; | 20.44 |

REFERENCE EXAMPLE 14

3-Amino-7-benzyl-5-propylpyrazolo[3,4-d]pyrimidine-4,6(5H,7H)-dione

3-Acetylamino-7-benzyl-5-propylpyrazolo[3,4-d]pyrimidine-4,6(5H,7H)-dione (18 g) was refluxed for 5 hours in 80% ethanol (200 ml) dissolving sodium hydroxide (6 g). The reaction mixture was concentrated, and the resulting crystals were suspended in water. To the suspension was added 6N-HCl to obtain colorless crystals (11 g, 70%), m.p. 214°–215° C.

Elemental Analysis for $C_{15}H_{17}N_5O_2$:

|  | C (%) | H (%) | N (%) |
|---|---|---|---|
| Calcd.: | 60.19; | 5.72; | 23.40 |
| Found: | 60.35; | 5.65; | 23.24 |

By a manner analogous to the above, the following compounds (REFERENCE EXAMPLEs 15 to 18) were synthesized.

REFERENCE EXAMPLE 15

3-Amino-7-(4-chlorobenzyl)-5-propylpyrazolo[3,4-d]pyrimidine-4,6(5H,7H)-dione, m.p. 208°–210° C.

REFERENCE EXAMPLE 16

3-Amino-7-(3-chlorobenzyl)-5-propylpyrazolo[3,4-d]pyrimidine-4,6(5H,7H)-dione, m.p. 141°–142° C.

REFERENCE EXAMPLE 17

3-Amino-7-(2-chlorobenzyl)-5-propylpyrazolo[3,4-d]pyrimidine-4,6[5H,7H)-dione, m.p. 263°–265° C.

REFERENCE EXAMPLE 18

3-Amino-5-benzyl-7-butylpyrazolo[3,4-d]pyrimidine-4,6(5H,7H)-dione, m.p. 197°–198° C.

REFERENCE EXAMPLE 19

3-Amino-7-benzyl-2-(2-chloroethyl)-5-propyl-2H-pyrazolo[3,4-d]pyrimidine-4,6(5H,7H)-dione A mixture of 3-amino-7-benzyl-5-propylpyrazolo[3,4-d]pyrimidine-4,6(5H,7H)-dione (11 g), 1-bromo-2-chloroethane (8.0 g) and potassium carbonate (7.0 g) was stirred in DMF (120 ml) at 50°–60° C. for 12 hours. The reaction mixture was concentrated to dryness, then the concentrate was extracted with chloroform/water. The chloroform layer was washed with water, dried and concentrated. The resultant brown syrup was purified by flash chromatography (silica gel 100 g, chloroform). The resultant syrup was crystallized from isopropylether to afford colorless needles (8.0 g, 60%), m.p. 126° to 128° C.

| Elemental Analysis for $C_{17}H_{20}N_5O_2Cl$: | | | |
|---|---|---|---|
| | C (%) | H (%) | N (%) |
| Calcd.: | 56.43; | 5.57; | 19.36 |
| Found: | 56.61; | 5.49; | 19.18 |

By a manner analogous to REFERENCE EXAMPLE 19, the following compounds (REFERENCE EXAMPLEs 20 to 25) were synthesized.

REFERENCE EXAMPLE 20

3-Amino-7-(4-chlorobenzyl)-2-(2-chloroethyl)-5-propyl-2H-pyrazolo[3,4-d]pyrimidine-4,6(5H,7H)-dione, m.p. 161°–163° C.

REFERENCE EXAMPLE 21

3-Amino-7-(3-chlorobenzyl)-2-(2-chloroethyl)-5-propyl-2H-pyrazolo[3,4-d] pyrimidine-4,6(5H,7H)-dione, m.p. 128°–130° C.

REFERENCE EXAMPLE 22

3-Amino-7-(2-chlorobenzyl)-2-(2-chloroethyl)-5-propyl-2H-pyrazolo[3,4-d]pyrimidine-4,6(5H,7H)-dione, m.p. 162°–165° C.

REFERENCE EXAMPLE 23

3-Amino-5-benzyl-7-butyl-2-(2-chloroethyl)-2H-pyrazolo[3,4-d]pyrimidine-4,6(5H,7H)-dione, m.p. 172°–173° C.

REFERENCE EXAMPLE 24

3-Amino-2-(2-chloroethyl)-7-phenethyl-5-propyl-2H-pyrazolo[3,4-d]pyrimidine-4,6(5H,7H)-dione, m.p. 276°–277° C.

REFERENCE EXAMPLE 25

3-Amino-2-(2-chloroethyl)-7-(3-phenylpropyl)-5-propyl-2H-pyrazolo[3,4-d]pyrimidine-4,6(5H,7H)-dione, m.p. 219°–220° C.

REFERENCE EXAMPLE 26

3-Amino-7-benzyl-2-(hexan-2-on-1-yl)-5-propyl-2Hpyrazolo[3,4-d]pyrimidine-4,6(5H,7H)-dione A mixture of
3-amino-7-benzyl-5-propylpyrazolo[3,4-d]pyrimidine-4,6(5H,7H)-dione (1 g), 1-chloro-2-hexanone (2 g) and potassium carbonate (2 g) in acetonitrile (50 ml) was stirred at room temperatures for 4 days. Insoluble material was filtered off. The filtrate was concentrated and the concentrate was washed with water and subsequently hexane to obtain pale brown powder (1.3 g, 98%). This product was used for the subsequent reaction without further purification.

$^1$H-NMR (CDCl$_3$) δ: 0.75–1.05 (6H,m), 1.05–2.20 (6H,m), 2.43 (2H,t), 3.85 (2H,t), 4.65 (2H,s), 5.05 (2H,s), 5.10 (2H,s), 7.20–7.50 (5H,m).

REFERENCE EXAMPLE 27

3-Amino-7-benzyl-2-(3-methoxyphenacyl)-5-propyl-2H-pyrazolo[3,4-d]pyrimidine-4,6(5H,7H)-dione A mixture of 3-amino-7-benzyl-5-propylpyrazolo[3,4-d]pyrimidine (1.0 g), p-methoxyphenacylbromide (2 g) and potassium carbonate (1 g) in acetonitrile (50 ml) was stirred for 3–4 days. Precipitating crystals in the mixture were collected by filtration and washed with water to obtain colorless crystals (1.16 g, 78%), m.p. 184°–185° C.

$^1$H-NMR (CDCl$_3$) δ: 0.90 (3H,t), 1.35–1.90 (2H,m), 3.80 (2H,t), 3.81 (3H,s), 5.05 (2H,s), 5.17 (2H,s), 5.27 (2H,s), 7.05–7.65 (9H,m).

By a manner analogous to REFERENCE EXAMPLE 27, the following compounds (REFERENCE EXAMPLEs 28 to 32) were synthesized.

REFERENCE EXAMPLE 28

3-Amino-7-benzyl-2-(2-methoxyphenacyl)-5-propyl-2H-pyrazolo[3,4-d]pyrimidine-4,6(5H,7H)-dione (m.p. 173°–174° C., 100%)

REFERENCE EXAMPLE 29

3-Amino-7-benzyl-2-(4-methoxyphenacyl)-5-propyl-2H-pyrazolo[3,4-d]pyrimidine-4,6(5H,7H)-dione (m.p. 205°–206° C., 89%)

REFERENCE EXAMPLE 30

3-Amino-7-benzyl-2-(4-chlorophenacyl)-5-propyl-2H-pyrazolo[3,4-d]pyrimidine-4,6(5H,7H)-dione (69%)

REFERENCE EXAMPLE 31

3-Amino-7-benzyl-2-(3-chlorophenacyl)-5-propyl-2H-pyrazolo[3,4-d]pyrimidine-4,6(5H,7H)-dione (61%)

REFERENCE EXAMPLE 32

3-Amino-7-benzyl-2-(4-butoxyphenacyl)-5-propyl-2H-pyrazolo[3,4-d]pyrimidine-4,6(5H,7H)-dione (m.p. 148°–149° C., 56%)

WORKING EXAMPLE 1

1-benzyl-3-propyl-1,2,3,4,6,7-hexahydro-5H-imidazo[2′,1′:5,1]pyrazolo[3,4-d]pyrimidine-2,4-dione Sodium hydride (60% oil, 0.8 g) was added in portions to a stirring solution of 3-amino-7-benzyl-2-(2-chloroethyl)-5-propyl-2H-pyrazolo[3,4-d]pyrimidine-4,6(5H,7H)-dione (4.9 g) under cooling with ice bath. The mixture was stirred for 17 hours and was concentrated to dryness. The residue was triturated with water and the resulting crystals were collected by filtration, washed with water and dried.

Recrystallization from DMF-methylene chloride gave colorless crystals (2.5 g, 57%), m.p. 215°–216° C.

| Elemental Analysis for $C_{17}H_{19}N_5O_2$: | | | |
|---|---|---|---|
| | C (%) | H (%) | N (%) |
| Calcd.: | 62.76; | 5.89; | 21.52 |
| Found: | 62.59; | 5.87; | 21.42 |

NMR(d$_6$-DMSO) δ: 0.90 (3H,t), 1.40–1.85 (2H,m), 3.87 (2H,t), 4.05 (4H,s), 5.07 (2H,s), 6.73 (1H,s), 7.20–7.55(5H,m).

The following compounds were synthesized by the same procedure as Working Example 1.

TABLE 1

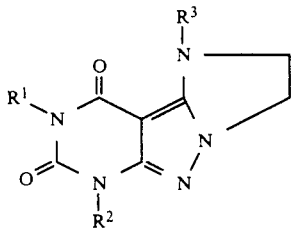

| W. Ex. No. | R$^1$ | R$^2$ | R$^3$ | Yield (%) | m.p. (°C.) | $^1$H-NMR Spectrum (Solvent) |
|---|---|---|---|---|---|---|
| 2 | Pr | —CH$_2$—⟨⟩—Cl | H | 51 | 236–238 | (d$_6$-DMSO) 0.90(3H, t), 1.40–1.85(2H, m), 3.87 (2H, t), 4.05(4H, s), 5.07(2H, s), 6.73 (1H, s), 7.20–7.55(5H, m) |
| 3 | Pr | —CH$_2$—⟨⟩Cl | H | 73 | 205–207 | (CDCl$_3$) 0.90(3H, t), 1.40–1.85(2H, m), 3.87 (2H, t), 4.10(4H, s), 5.05(2H, s), 5.40–5.90(1H, br s), 7.10–7.35(3H, m), 7.40(1H, s) |
| 4 | Pr | —CH$_2$—⟨⟩Cl | H | 55 | 262–263 | (d$_6$-DMSO) 0.90(3H, t), 1.35–1.80(2H, m), 3.87 (2H, t), 4.03(4H, s), 5.17(2H, s), 6.85–7.45(5H, m) |
| 5 | —CH$_2$—⟨⟩ | Bu | H | 72 | 156–157 | (CDCl$_3$) 0.93(3H, t), 1.15–1.93(4H, m), 3.80–4.25(6H, m), 5.10(2H, s), 5.80(1H, s), 7.20–7.50(5H, m) |
| 6 | Pr | —CH$_2$CH$_2$—⟨⟩ | H | 94 | 209–210 | |

TABLE 1-continued

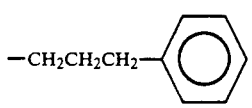

| W. Ex. No. | R¹ | R² | R³ | Yield (%) | m.p. (°C.) | ¹H-NMR Spectrum (Solvent) |
|---|---|---|---|---|---|---|
| 7 | Pr | —CH₂CH₂CH₂—C₆H₅ | H | 99 | 138–139 | |

WORKING EXAMPLE 8

1-Benzyl-3-propyl-1,2,3,4-tetrahydro-5H-imidazo[2′,1′:5,1]pyrazolo[3,4-d]pyrimidine-2,4-dione A solution of 1-benzyl-3-propyl-1,2,3,4,6,7-hexahydro-5H-imidazo [2′,1′: 5,1]- pyrazolo[3,4-d]pyrimidine-2,4-dione (4.5 g) and benzoyl peroxide (5.0 g) in chloroform (100 ml) was refluxed for 18 hours. The reaction mixture was concentrated to dryness, and the residue was dissolved in chloroform. The solution was washed with an aqueous solution of sodium carbonate and water, followed by drying and concentration to dryness. The residue was purified by flash chromatography. Recrystallization of thus obtained crystals from methylene chloride/hexane afforded colorless crystals (2.3 g, 52%), m.p. 290°–292° C.

| Elemental Analysis for $C_{17}H_{17}N_5O_2$: | | | |
|---|---|---|---|
| | C (%) | H (%) | N (%) |
| Calcd.: | 63.15; | 5.30; | 21.66 |
| Found: | 63.38; | 5.19; | 21.50. |

$^1$H-NMR(d$_6$-DMSO) δ: 0.91(3H,t), 1.45–1.90(2H,m), 3.93(2H,t), 5.20(2H,s), 6.93(1H,s), 7.20–7.60(6H,m), 12.45(1H,s)

The following compounds were synthesized by the same procedure as Working Example 8.

TABLE 2

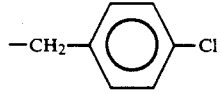

| W. Ex No. | R¹ | R² | Yield (%) | m.p. (°C.) | ¹H-NMR Spectrum (Solvent) |
|---|---|---|---|---|---|
| 9 | Pr | —CH₂—C₆H₄—Cl (para) | 51 | 288–290 | (d₆-DMSO) 0.87(3H, t), 1.30–1.80(2H, m), 3.87(2H, t), 5.10(2H, s), 7.10–7.50(5H, m), 7.70(1H, d) |
| 10 | Pr | —CH₂—C₆H₄—Cl (meta) | 50 | 278–280 | (d₆-DMSO) 0.87(3H, t), 1.35–1.85(2H, m), 3.87(2H, t), 5.15(2H, s), 7.37(4H, s), 7.43(1H, s), 7.79 (1H, d) |
| 11 | Pr | —CH₂—C₆H₄—Cl (ortho) | 47 | >300 | (d₆-DMSO) 0.87(3H, t), 1.35–1.85(2H, m), 3.87(2H, t), 5.20(2H, s), 6.90–7.10(1H, m), 7.10–7.40(3H, m), 7.40–7.60(1H, m), 7.70(1H, d) |
| 12 | —CH₂—C₆H₅ | Bu | 60 | 250–251 | (d₆-DMSO) 0.90(3H, t), 1.10–1.50(2H, m), 1.50–1.90(2H, m), 3.93(2H, t), 5.07(2H, s), 7.27(6H, s), 7.77(1H, d), 12.83(1H, s) |

TABLE 2-continued

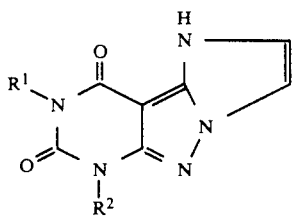

| W. Ex No. | R¹ | R² | Yield (%) | m.p. (°C.) | ¹H-NMR Spectrum (Solvent) |
|---|---|---|---|---|---|
| 13 | Pr | —CH₂CH₂—⟨phenyl⟩ | 60 | 276–277 | (d₆-DMSO) 0.90(3H, t), 1.40–1.90(2H, m), 3.00–3.25(2H, m), 3.95(2H, t), 4.17–4.40(2H, m), 6.97(1H, d) 7.30(5H, s), 7.39(1H, d), 12.45(1H, s) |
| 14 | Pr | —CH₂CH₂CH₂—⟨phenyl⟩ | 59 | 219–220 | (CDCl₃) 1.00(3H, t), 1.50–2.00(2H, m), 2.0–2,4(2H, m) 2.6–2.9(2H, m), 4.03(2H, t), 4.17(2H, t), 6.90 (1H, t), 7.20(5H, s), 7.37(1H, d), 12.03(1H, s) |

WORKING EXAMPLE 15

1-Benzyl-3-propyl-6-phenyl-1,2,3,4-tetrahydro-5H-imidazo [2',1':5,1]pyrazolo[3,4-d]pyrimidine-2,4-dione A suspension of 3-amino-7-benzyl-5-propylpyrazolo [3,4-d]pyrimidine-4,6(5H,7H)-dione (2.0 g), phenacyl chloride (4.4 g), K₂CO₃ (2.5 g) and potassium iodide (1.4 g) in acetonitrile (150 ml) was stirred for 3 days at room temperature. Precipitating crystals were collected by filtration and washed with water. The filtrate was concentrated to give a syrup. The syrup was crystallized by the addition of isopropyl ether. The crystals were combined and dissolved in toluene (200 ml). To the solution was added p-toluenesulfonic acid (0.1 g), followed by heating for 3 hours under reflux. The reaction mixture was concentrated to dryness and then was added isopropyl ether to give crude crystals, followed by recrystallization from methanol to afford colorless crystals (1.1 g, 43%), m.p. 261°–262° C.

| Elemental Analysis for C₂₃H₂₁N₅O₂: | | | |
|---|---|---|---|
| | C (%) | H (%) | N (%) |
| Calcd.: | 69.15; | 5.30; | 17.53 |
| Found: | 69.04; | 5.44; | 17.69. |

¹H-NMR(d₆-DMSO) δ: 0.91(3H,t), 1.40–1.90(2H,m), 3.95(2H,t), 5.21(2H,s), 7.10–7.85(11H,m)

The following compounds were synthesized by the same procedure as Working Example 15.

TABLE 3

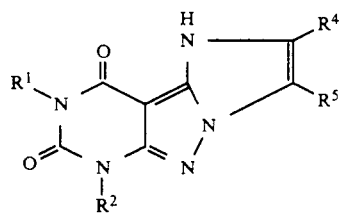

| W. Ex. No. | R¹ | R² | R⁴ | R⁵ | Yield (%) | m.p. (°C.) | ¹H-NMR Spectrum (Solvent) |
|---|---|---|---|---|---|---|---|
| 16 | Pr | —CH₂—⟨phenyl⟩ | Me | Me | 63 | >300 | (d₆-DMSO) 0.90(3H, t), 1.40–1.90(2H, m), 2.27 (3H, s), 2.31(3H, s), 3.90(2H, t), 5.20 (2H, s), 7.15–7.40(3H, m), 7.40–7.57 (2H, m), 12.17(1H, s) |
| 17 | Pr | —CH₂—⟨phenyl⟩ | Bu | H | 71 | 208–209 | (CDCl₃) 0.85(3H, t), 0.93(3H, t), 1.10–2.00 (6H, m), 2.67(2H, t), 4.00(2H, t), 5.27 (2H, s), 7.07(1H, s), 7.20–7.40(3H, m) 7.40–7.65(2H, m), 11.30(1H, s) |
| 18 | Pr | —CH₂—⟨phenyl⟩ | —⟨biphenyl⟩ | H | 25 | 265–266 | |

TABLE 3-continued

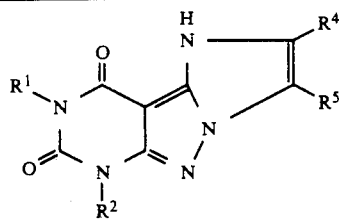

| W. Ex. No. | R¹ | R² | R⁴ | R⁵ | Yield (%) | m.p. (°C.) | ¹H-NMR Spectrum (Solvent) |
|---|---|---|---|---|---|---|---|
| 19 | Pr | —CH₂—C₆H₅ | (cyclohexylidene) | | 6 | 300–302 | (CDCl₃) 0.90(3H, t), 1.30–2.10(6H, m), 2.45–2.85(4H, m), 3.90(2H, t), 5.20(2H, s) 7.15–7.70(5H, m), 12.07(1H, s) |
| 20 | Pr | —CH₂—C₆H₅ | C₆H₅ | H | 52 | 307–309 | (d₆-DMSO) 0.93(3H, t), 1.40–1.90(2H, m), 3.95 (2H, t), 5.20(2H, s), 7.15–7.80(9H, m) 7.63(1H, s), 12.95(1H, s) |

WORKING EXAMPLE 21

1-Benzyl-6-(3-methoxyphenyl)-3-propyl-1,2,3,4-tetrahydro-5H-imidazo[2',1':5,1]pyrazolo[3,4-d]pyrimidine-2,4-dione 3-Amino-7-benzyl-2-(3-methoxyphenacyl)-5-propyl-2H-pyrazolo[3,4-d]pyrimidine-4,6(5H,7H)-dione (1.16 g) and p-toluenesulfonic acid (0.1 g) were dissolved in toluene (50 ml) and the solution was refluxed for 3 hours. The reaction solution was concentrated and to the concentrate was added methanol. Precipitating crystals were collected by filtration to obtain pale yellow crystals (0.83 g, 75%), m.p. 249°–250° C.

| Elemental Analysis for C₂₄H₂₃N₅O₃: | | | |
|---|---|---|---|
| | C (%) | H (%) | N (%) |
| Calcd.: | 67.12; | 5.40; | 16.31 |
| Found: | 67.43; | 5.24; | 16.05 |

¹H-NMR(CDCl₃+d₆-DMSO) δ: 0.90(3H,t), 1.40–1.90(2H,m), 3.80(3H,s), 3.93(2H,t), 5.17(2H,s), 6.70–7.65(10H,m), 12.90(1H,s)

The following compounds were synthesized by the same procedure as Working Example 21.

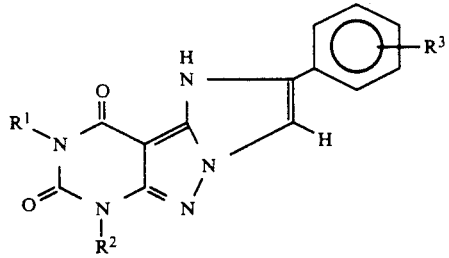

| W. Ex. No. | R¹ | R² | R³ | Yield (%) | m.p. (°C.) | ¹H-NMR spectrum (solvent) |
|---|---|---|---|---|---|---|
| 22 | Pr | —CH₂—C₆H₅ | p-MeO | 69 | 275–276 | (d₆-DMSO) 0.90(3H, t), 1.40–1.90(2H, m), 3.77(3H, s), 3.93(2H, t), 5.19(2H, s), 6.90(2H, d), 7.60 (2H, d), 7.43(1H, s), 7.20–7.35(3H, m), 7.35–7.50(2H, m), 12.70(1H, s) |
| 23 | Pr | —CH₂—C₆H₅ | o-MeO | 88 | 112–113 | (CDCl₃) 0.87(3H, t), 1.40–1.90(2H, m), 3.90(2H, t), 3.90(3H, s), 5.20(2H, s), 6.80–7.70(10H, m), 11.07(1H, s) |
| 24 | Pr | —CH₂—C₆H₅ | p-BuO | 81 | 108–109 | (CDCl₃) 0.80(3H, t), 0.95(3H, t), 1.20–1.95(6H, m), 2.33(3H, s), 3.87(2H, t), 3.93(2H, t), 5.20(2H, s), 6.85(2H, d), 7.20–7.60(8H, m), 11.75(1H, s), |

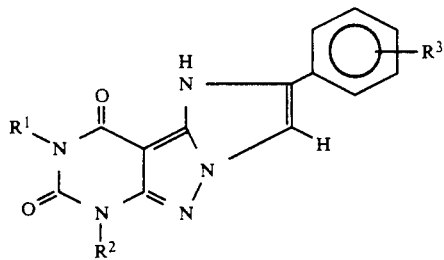

| W. Ex. No. | $R^1$ | $R^2$ | $R^3$ | Yield (%) | m.p. (°C.) | $^1$H-NMR spectrum (solvent) |
|---|---|---|---|---|---|---|
| 25 | Pr | —CH$_2$–C$_6$H$_5$ | p-Me | 48 | 261–262 | (CDCl$_3$) 0.78(3H, t), 1.30–1.80(2H, m), 2.33(3H, s), 3.80(2H, t), 5.20(2H, s), 7.00–7.60 (10H, m), 11.50(1H, s) |
| 26 | Pr | —CH$_2$–C$_6$H$_5$ | m-Cl | 52 | 247–248 | (d$_6$-DMSO) 0.93(3H, t), 1.40–1.90(2H, m), 3.93(2H, s), 5.20(2H, s), 7.17–7.90(10H, m), 13.07 (1H, s) |
| 27 | Pr | —CH$_2$–C$_6$H$_5$ | o-Cl | 60 | 164–165 | (CDCl$_3$-CD$_3$OD) 0.97(3H, t), 1.40–1.90(2H, m), 4.00(2H, s), 5.27(2H, s), 7.30–7.87(10H, m) |
| 28 | Pr | —CH$_2$–C$_6$H$_5$ | p-Cl | 70 | 307–309 | (d$_6$-DMSO) 0.93(3H, t), 1.40–1.90(2H, m), 3.95(2H, t), 5.20(2H, s), 7.15–7.80(9H, m), 7.63 (1H, s), 12.95(1H, s) |

WORKING EXAMPLE 29

1-Butyl-1,2,3,4,6,7-hexahydro-5H-imidazo[2',1':5,1-]pyrazolo[3,4-d]pyrimidine-2,4-dione Boron tribromide (0.35 ml) was added to a stirred suspension of 3-benzyl-1-butyl-1,2,3,4,6,7-hexahydroimidazo[2',1':5,1]pyrazolo[3,4-d]pyrimidine2,4-dione (0.5 g) at room temperature. The reaction mixture was refluxed for 19 hours and there was cooled to room temperature, followed by addition of methanol (5 ml). The mixture was stirred for a while, then concentrated to dryness. The residue was dissolved in ethyl acetate, washed with water, dried and concentrated to give crude crystals, followed by recrystallization from ethyl acetate/hexane to afford colorless crystals (0.1 g, 27%), m.p. 239°–240° C.

| Elemental Analysis for C$_{11}$H$_{15}$N$_5$O$_2$: | | | |
|---|---|---|---|
| | C (%) | H (%) | N (%) |
| Calcd.: | 53.00; | 6.07; | 28.10 |
| Found: | 53.24; | 6.11; | 27.86 |

$^1$H-NMR(d$_6$-DMSO) δ: 0.93(3H,t), 1.10–1.90(4H,m), 3.87(2H,t), 4.10(4H,s), 6.90(1H,s), 9.73(1H,s).

WORKING EXAMPLE 30

3-Propyl-1,2,3,4-tetrahydro-5H-imidazo[2',1':5,1-]pyrazolo[3,4-d]pyrimidine-2,4-dione Boron tribromide (0.35 ml) was added to a stirred suspension of 1-benzyl-3-propyl-1,2,3,4-tetrahydro-5H-imidazo [2',1':5,1]pyrazolo[3,4-d]pyrimidine-2,4-dione (0.5 g) at room temperature. The reaction mixture was refluxed for 22 hours and then cooled to room temperature, followed by addition of methanol (10 ml). The mixture was stirred for a while and was concentrated to dryness. After addition of ethyl acetate, resulting crystals were collected by filtration and washed with water to give crude crystals. Recrystallization from ethyl acetate gave colorless crystals (0.16 g, 44%), m.p. 326°–328° C. (decomp.).

| Elemental Analysis for C$_{10}$H$_{11}$N$_5$O$_2$: | | | |
|---|---|---|---|
| | C (%) | H (%) | N (%) |
| Calcd.: | 51.49; | 4.75; | 30.03 |
| Found: | 51.10; | 4.83; | 29.84 |

$^1$H-NMR(d$_6$-DMSO) δ: 0.87(3H,t), 1.30–1.80(2H,m), 3.83(2H,t), 7.20(1H,s), 7.60(1H,s), 11.40(1H,s), 12.67(1Hs).

WORKING EXAMPLE 31

1-Benzyl-6-butyl-5-methyl-3-propyl-1,2,3,4-tetrahydro-5H-imidazo [2',1':5,1]pyrazolo[3,4-d]pyrimidine-2,4-dione In DMF (20 ml) was dissolved 1-benzyl-6-butyl-3-propyl-1,2,3,4-tetrahydro-5H-imidazo [2',1':5,1]pyrazolo[3,4-d]pyrimidine-2,4-dione (0.5 g). To the solution were added, at room temperature, K$_2$CO$_3$ (0.5 g) and methyl iodide (0.5 g). The mixture was stirred for 8 hours and concentrated to dryness. To the residue was added water, then precipitating crystals were recrystallized from aqueous methanol to give colorless crystals (0.51 g, 98%), m.p. 139°–140° C.

| Elemental Analysis for $C_{22}H_{27}N_5O_2$: | | | |
|---|---|---|---|
| | C (%) | H (%) | N (%) |
| Calcd.: | 67.15; | 6.92; | 17.80 |
| Found: | 66.92; | 6.78; | 17.65 |

$^1$H-NMR(CDCl$_3$) δ: 0.93(6H,t), 1.20–1.90(6H,m), 2.60(2H,t), 3.95(2H,t), 4.00(3H,s), 5.20(2H,s), 7.05(1H,s), 7.20–7.40(3H,m), 7.40–7.60(2H,m).

WORKING EXAMPLE 32

1-Benzyl-6-cyclopropyl-3-propyl-1,2,3,4-tetrahydro-5H-imidazo[2',1':5,1]pyrazolo[3,4-d]pyrimidine-2,4-dione 3-Amino-7-benzyl-2-(5-chloro-2-oxopentyl)-5-propylpyrazolo[3,4-d]pyrimidine-4,6(5H,7H)-dione (0.8 g) was suspended in methanol (20 ml). To the suspension was added a solution of 28% NaOMe in methanol (4 ml). The mixture was stirred at room temperature for 30 minutes and then at 60° C. for 3 hours. The reaction solution was concentrated to dryness. The residue was dissolved in methylene chloride, washed with water and concentrated to dryness to obtain crude crystals. Recrystallization from isopropyl ether gave colorless crystals (0.52 g), m.p. 264°–265° C.

| Elemental Analysis for $C_{20}H_{21}N_5O_2$: | | | |
|---|---|---|---|
| | C (%) | H (%) | N (%) |
| Calcd.: | 66.10; | 5.82; | 19.27 |
| Found: | 66.48; | 5.84; | 19.07 |

WORKING EXAMPLE 33

1-Benzyl-6-dimethylaminomethyl-3-propyl-1,2,3,4-tetrahydro-5H-imidazo
[2',1':5,1]pyrazolo[3,4-d]pyrimidine-2,4-dione 1-Benzyl-3-propyl-1,2,3,4-tetrahydro-5H-imidazo[2',1':5,1]pyrazolo[3,4-d]pyrimidine-2,4-dione (1.6 g) was dissolved in 80% acetic acid (18 ml). To the solution were added paraformaldehyde (0.57 g) and dimethylamine (50% aqueous solution, 1.73 g). The mixture was stirred at 70° C. for 2 hours. The reaction solution was concentrated to dryness. To the residue were added methylene chloride (50 ml), water (50 ml), 2N-hydrochloric acid (5 ml) and acidic sodium bisulfite (2 g) and the mixture was stirred at room temperature for 15 hours. To the mixture was added sodium hydrogen carbonate to render it to weak alkali. The organic layer was washed with water, dried and concentrated to obtain a mixture of 6-dimethylamino compound and 7-dimethylamino compound. Recrystallization from ethanol gave 6-dimethylamino compound.

WORKING EXAMPLE 34

1-Benzyl-7-dimethylaminomethyl-3-propyl-1,2,3,4-tetrahydro-5H-imidazo
[2',1':5,1]pyrazolo[3,4-d]pyrimidine-2,4-dione A mixture of 6-dimethylaminomethyl compound and 7-dimethylaminomethyl compound was obtained by the same procedure as Working Example 33. Recrystallization from ethanol gave 7-dimethylaminomethyl compound.

EXAMPLES OF PHARMACEUTICAL PREPARATIONS

When a compound (I) of the present invention is intended for use as a therapeutic and prophylactic agent, owing to its properties of ameliorating cerebral functions and activating cerebral metabolisms which are decreased by the occurrence of cerebrovascular disease, brain injury or aging, of, for example, dementia caused by cerebral apoplexy, brain injury or cerebral atrophy, the compound can be used in forms of, for example, the following prescriptions.

| 1. Tablet | |
|---|---|
| (1) 1-Benzyl-3-propyl-1,2,3,4-tetrahydro-5H-imidazo-[2',1':5,1]pyrazolo[3,4-d]pyrimidine-2,4-dione | 10 mg |
| (2) Lactose | 35 mg |
| (3) Corn starch | 150 mg |
| (4) Microcrystalline cellulose | 30 mg |
| (5) Magnesium stearate | 5 mg |
| | 230 mg |

The whole amount each of (1), (2) and (3), together with two thirds of the amount of (4) and a half of the amount of (5), are mixed and then granulated. The residual amounts of (4) and (5) are added to the granules and compressed into a tablet.

| 2. Capsule | |
|---|---|
| (1) 1-Benzyl-6-phenyl-3-propyl-1,2,3,4-tetrahydro-5H-imidazo[2',1':5,1]pyrazolo[3,4-d]pyrimidine-2,4-dione | 10 mg |
| (2) Lactose | 100 mg |
| (3) Microcrystalline cellulose | 70 mg |
| (4) Magnesium stearate | 10 mg |
| | 190 mg |

The whole amount each of (1), (2) and (3), together with a half of the amount of (4), are mixed and then granulated. The residual amount of (4) is added to the granules, and the mixture is filled into a gelatine capsule.

EXPERIMENTAL EXAMPLE 1

Adenosine Antagonism

Preparation of membranes was performed in accordance with the method of Burns et al. described in Proc. Natl. Acad. Sci., 77, 5547 (1980). More specifically, a rat was decapitated, and the cerebral cortex ($A_1$ receptor) or corpus striatun ($A_2$ receptor) was suspended using Polyton in a Tris-HCl buffer solution of pH 7.7 (50 mM, 20 ml). This suspension was centrifuged at 48,000 g for 10 minutes, and the pellet was resuspended and centrifuged in a similar manner. The pellet was resuspended in a Tris-HCl buffer solution (50 mM), to which was added adenosine deaminase (2U/ml). The mixture was incubated at 37° C. for 30 minutes. This suspension was centrifuged and the pellet was stored at −20° C.

Using the above-mentioned pellet, adenosine antagonism ($A_1$ and $A_2$) was examined.

1) $A_1$ receptor antagonism

The above-mentioned pellet was thawed at room temperature and suspended in a Tris-HCl buffer solution. To the suspension (0.9 ml) were added $^3$H-cyclohexyladenosine ($^3$H-CHA)(ca. 0.05 μCi, 0.1 ml)

and the test drug (10 μl), and the mixture was incubated at 25° C. for 60 minutes. The reaction mixture was subjected to filtration with GF/B filter. The filter was washed four times with a Tris-HCl buffer solution. The radioactivity on the filter was measured by liquid scintillation. The nonspecific binding amount was measured in the presence of $10^{-5}M$ of L-phenyl isopropyladenosine.

2) $A_2$ receptor antagonism

The experiment was performed analogously to that for $A_1$ receptor antagonism. Using $^3$H-adenosine-5'-ethylcarboxamide ($^3$H-NECA; about 0.1 μCi) as ligand, the experiment was conducted in the presence of 50 nM of cyclopentyladenosine. The nonspecific binding amount was measured in the presence of $10^{-4}M$ of cyclopentyladenosine.

The results of these $A_1$ and $A_2$ receptor antagonism are shown in Table 4.

TABLE 4

Inhibitory Action of Adenosine Receptor Binding
The action was shown in terms of binding-inhibition constants (Ki, μM).

| Working Example | $A_1$ receptor (Ki, μM) | $A_2$ receptor (Ki, μM) |
|---|---|---|
| 1 | 0.12 | 3.3 |
| 2 | 0.14 | 2.9 |
| 3 | 0.19 | 4.2 |
| 4 | 0.27 | 6.5 |
| 5 | 0.67 | 4.5 |
| 8 | 0.034 | 0.26 |
| 9 | 0.050 | 0.37 |
| 10 | 0.098 | 0.46 |
| 11 | 0.092 | 1.0 |
| 12 | 0.20 | 1.1 |
| 13 | 0.53 | 16.0 |
| 14 | 0.11 | 2.5 |
| 15 | 0.01 | 0.28 |
| 16 | 0.024 | 0.43 |
| 17 | 0.0051 | 0.35 |
| 19 | 0.027 | 0.19 |
| 20 | 0.013 | 1.1 |
| 21 | 0.0069 | 0.12 |
| 22 | 0.0047 | 0.21 |
| 23 | 0.53 | 0.50 |
| 24 | 0.053 | >0.5 |
| 25 | 0.58 | >0.5 |
| 26 | 0.037 | >0.5 |
| 27 | 0.58 | >0.5 |
| 29 | 18.0 | 39.0 |
| 30 | 0.42 | 0.42 |

EXPERIMENTAL EXAMPLE 2

Action of ameliorating retention deficit induced by an anticholinergic, scopolamine Actions of the compound (8) obtained in Working Example 8 and the compound (9) obtained in Working Example 9 on amelioration of memory impairment was studied using the passive avoidance task shown below. Five-week old male mice were placed first in the light chamber of a passive avoidance learning apparatus consisting of light and dark chambers. The mice immediately moved into the dark chamber, then an unescapable electric shock (0.5 mA, 3 sec.) was applied to the animals. These animals retained for several weeks the memory that they received the electric shock. This memory retention was disrupted by the following procedure, and the effect of the compounds (8) and (9) was tested. Thirty minutes prior to the application of electric shock, these animals were each administered with scopolamine (1 mg/kg, i.p), then these mice lost the memory of this experience of an electric shock.

On the following day, a retention recovery test was conducted. These mice were again placed in the light chamber of the passive avoidance apparatus and the time until the animals moved into the dark chamber (avoidance time) was measured. These mice which lost the memory of the experience of an electric shock moved again into the dark chamber in 10 to 20 seconds. On the other hand, the mice orally administered a 5% gum arabic suspension of the compound (8) or (9) recovered the memory, and they would not move into the dark chamber or took a long time before they moved there. The effects of these test compounds were examined by comparing the average value (11-15 animals/group) of the period of time during which the mice stayed in the light chamber with that of the control group (administered only a suspension of 5% gum arabic containing no test compound). The results were expressed by the percent change rate relative to the mean value (100) in the control group (Table 5).

Table 5 shows ameliorating effects of the compounds (8) and (9) on retention deficit induced by scopolamine.

TABLE 5

Ameliorating Effects on Retention Deficit Induced by Scopolamine (1 mg/kg, i.p.)

| Working Example No. | Administration Route | Dosage (mg/kg) | Avoidance Time (%) |
|---|---|---|---|
| Control Group | p.o. | — | 100 |
| 8 | p.o. | 3 | 243* |
| 9 | p.o. | 3 | 262* |

*$P < 0.05$ (comparison with the control group)

EXPERIMENTAL EXAMPLE 3

Action on depression of cerebral functions induced by experimental ischemia 3-1 Action of accelerating recovery of motility Experimental cerebral ischemia was produced in accordance with the method of Pulsinelli et al. (Stroke 10, 267-272, 1979), using Wistar rats 8-week old. On the first day of the experiment, the rats were anesthetized with pentobarbital, and their occipital skin and muscle were incised along the median line, then their vertebral arteries were cauterized bilaterally, and their ventral necks were incised, the bilateral common carotid arteries were separated from the surrounding tissue, to which a thread was applied. On the next day, the common carotid arteries were drawn out by the use of this thread under anaesthetic conditions, and occluded with clips for 30 minutes. By this treatment, serious cerebral ischemia was induced. After 30 minutes' occlusion, the clip was removed to allow the cerebral circulation to resume. Time to recovery of righting reflex and time to reappearance of spontaneous motor activity were measured on individual test animals. The test compound was orally administered to the animals as a 5% suspension in gum arabic one hour before causing the cerebral ischemia and immediately after the resumption of cerebral circulation. The control group was orally administered with only a 5% gum arabic suspension.

As shown in Table 6, the compound (8) tended to shorten the time to recovery of righting reflex dosedependently and shortened the time to reappearance of spontaneous motor activity. In the latter's index, the high dose of the compound (8) showed statistically significant action. Incidentally, this motility depression has a close relation to the depression of consciousness level. From these data, it was revealed that the compound (8) accelerated the recovery from disorders of cerebral functions caused by cerebral ischemia.

TABLE 6

Action of recovering from motility depression (depression of consciousness level) associated with cerebral ischemia

| Working Example No. | Number of animals | Time to recovery of righting reflex (min.) | Time to reappearance of spontaneous motility (min.) |
| --- | --- | --- | --- |
| Control group | 15 | 29.8 ± 5.9 | 81.5 ± 13.3 |
| Compound (8) | | | |
| 3mg/kg | 20 | 21.0 ± 3.2 | 55.2 ± 6.5 |
| 10mg/kg | 23 | 16.7 ± 2.6 | 43.8 ± 4.7* |

The data are shown in terms of average values and standard errors.
*P < 0.05 (comparison with the control group)

3-2 Action of ameliorating impaired learning

As in the case of the above test (3-1), Wistar rats were used to produce an experimental model for cerebral ischemia. In this experiment, the time during which cerebral ischemia was caused in the animals was 5 minutes. By this treatment, a passive avoidance learning impairments was induced. The passive avoidance learning was tested in accordance with the method in Experiment 1. The test compound was suspended in a 5% gum arabic vehicle. Test animals were administered with this suspension three times, i.e. one hour prior to causing cerebral ischemia, two hours prior to a passive avoidance learning and two hours prior to the test. The control group was administered with only a 5% gum arabic suspension. As shown in Table 7, the compound (8) prolonged the avoidance time, in the doses of 3 mg/kg and 10 mg/kg, dose-dependently. These data suggest that the compounds of the present invention show an action of ameliorating depression of cerebral functions associated with cerebral ischemia.

TABLE 7

Ameliorating action on impaired learning after cerebral ischemia

| | Number of animals | Avoidance time |
| --- | --- | --- |
| Control group | 9 | 17.5 (sec.) |
| Compound (8) | | |
| 3 mg/kg | 7 | 152.8 |
| 10 mg/kg | 10 | 285.9* |

Data are shown in terms of median value.
*P < 0.05 (comparison with the control group)

EXPERIMENTAL EXAMPLE 4

Acute toxicity

A group of 5 male Jcl:Wistar rats (9 week old, Japan Clea) and a group of 5 male Jcl:ICR mice (5 week old, Japan Clea) were used. These rats were each administered orally 500 mg and 1000 mg/kg/3 ml of the test compound, while these mice were each administered orally 600 mg and 2000 mg/kg/2 ml of the test compound. These oral administrations were made in the form of a suspension in 5% gum arabic vehicle. Twenty four hours later, the number of dead animals were counted. The results are shown in Table 8.

TABLE 8

| Animals | Dosage (mg/kg, p.o.) | Number of dead animals |
| --- | --- | --- |
| Rats | 500 | 0 |
| | 1000 | 0 |
| Mice | 600 | 0 |
| | 2000 | 0 |

What is claimed is:

1. A compound of the formula:

$$\text{(I)}$$

wherein either one of $R^1$ and $R^2$ is an optionally substituted aralkyl group and the other is hydrogen, an optionally substituted aralkyl group or an aliphatic hydrocarbon group; $R_3$ is hydrogen, an aliphatic hydrocarbon group or acyl group; and A is an optionally substituted divalent hydrocarbon chain having 2 to 4 carbon atoms or a pharmacologically acceptable salt thereof.

2. A compound according to claim 1, wherein the optionally substituted aralkyl group shown by $R^1$ or $R^2$ is an alkylene group having 1 to 4 carbon atoms combined with an aromatic hydrocarbon group being unsubstituted or substituted with 1 to 3 substituents selected from the class consisting of halogen, a lower ($C_{1-4}$) alkyl, a lower ($C_{1-4}$) alkoxy, nitro, amino N-lower ($C_{1-4}$) alkylamino, N,N-dilower ($C_{1-4}$) alkylamino, hydroxy, trifluoromethyl, carbamoyl, N-lower ($C_{1-4}$) alkylcarbamoyl and N,N-dilower ($C_{1-4}$) alkylcarbamoyl.

3. A compound according to claim 2, wherein the aromatic hydrocarbon group is phenyl or naphthyl.

4. A compound according to claim 2, wherein the aromatic hydrocarbon group is phenyl.

5. A compound according to claim 2, wherein the substituents are those selected from the class consisting of halogen, lower ($C_{1-4}$) alkyl, lower ($C_{1-4}$) alkoxy, nitro and amino.

6. A compound according to claim 1, wherein the aliphatic hydrocarbon group shown by $R^1$ or $R^2$ is a $C_{1-8}$ alkyl group or $C_{2-8}$ alkenyl group.

7. A compound according to claim 1, wherein the aliphatic hydrocarbon group shown by $R^1$ or $R^2$ is a $C_{2-5}$ aliphatic hydrocarbon group.

8. A compound according to claim 1, wherein the aliphatic hydrocarbon group shown by $R^1$ or $R^2$ is a $C_{2-5}$ alkyl group.

9. A compound according to claim 1, wherein either one of $R^1$ and $R^2$ is an optionally substituted aralkyl group and the other is an optionally substituted aralkyl group or an aliphatic hydrocarbon group.

10. A compound according to claim 1, wherein $R^1$ is an aliphatic hydrocarbon group and $R^2$ is an optionally substituted aralkyl group.

11. A compound according to claim 1, wherein the aliphatic hydrocarbon group shown by $R^3$ is $C_{1-3}$ alkyl group or $C_{2-3}$ alkenyl group.

12. A compound according to claim 1, wherein the aliphatic hydrocarbon group shown by $R^3$ is $C_{1-3}$ alkyl group.

13. A compound according to claim 1, wherein the acyl group is a $C_{2-7}$ alkanoyl group, aromatic carbonyl group, $C_{2-5}$ alkoxycarbonyl group, carbamoyl or formyl.

14. A compound according to claim 1, wherein the acyl group is a $C_{2-7}$ alkanoyl group or $C_{2-5}$ alkoxycarbonyl group.

15. A compound according to claim 1, wherein the acyl group is acetyl, propionyl or methoxycarbonyl.

16. A compound according to claim 1, wherein the divalent hydrocarbon chain having 2 to 4 carbon atoms is $C_{2-4}$ alkylene or $C_{2-4}$ alkenylene.

17. A compound according to claim 1, wherein A is a divalent straight hydrocarbon chain having 2 to 4 carbon atoms unsubstituted or substituted with 1 to 2 substituents selected from the class consisting of an optionally substituted aliphatic hydrocarbon group, an optionally substituted aromatic hydrocarbon group, halogen, nitro, amino and oxo.

18. A compound according to claim 17, wherein the optionally substituted aliphatic hydrocarbon group is a $C_{1-8}$ alkyl group unsubstituted or substituted with a member selected from the class consisting of an optionally substituted amino, nitro, hydroxy, $C_{1-4}$ alkoxy and $C_{1-4}$ alkylthio.

19. A compound according to claim 17, wherein the optionally substituted aromatic hydrocarbon group is phenyl unsubstituted or substituted with 1 to 2 substituents selected from the class consisting of an optionally substituted amino, nitro, hydroxy, methoxy, methyl and phenyl.

20. A compound according to claim 1, wherein A is $C_{2-4}$ alkylene; a hydrocarbon chain of the formula:

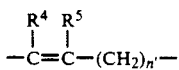

wherein $R^4$ and $R^5$ are independently hydrogen, an optionally substituted aliphatic hydrocarbon group, an optionally substituted aromatic hydrocarbon group or halogen, or $R^4$ and $R^5$ are combined to form a cyclic aliphatic hydrocarbon group having 5 to 8 carbon atoms of the formula:

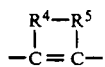

and n' is an integer of 0 to 2; or a hydrocarbon chain of the formula:

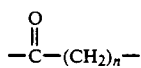

wherein n is an integer of 1 to 3.

21. A compound according to claim 1, wherein A is ethylene or a group of the formula:

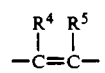

wherein $R^4$ and $R^5$ are independently hydrogen, phenyl unsubstituted or substituted with halogen or lower $(C_{1-4})$ alkoxy, or $C_{1-4}$ alkyl unsubstituted or substituted with amino, dimethylamino or morpholino.

22. A compound according to claim 1, wherein $R^1$ is a $C_{2-5}$ aliphatic hydrocarbon group; $R^2$ is a phenyl-lower $(C_{1-4})$ alkyl group, said phenyl group being unsubstituted or substituted with 1 to 3 substituents selected from the class consisting of halogen, a lower $(C_{1-4})$ alkyl, a lower $(C_{1-4})$ alkoxy, nitro, amino, N-lower $(C_{1-4})$ alkylamino, N,N-di-lower $(C_{1-4})$ alkylamino, hydroxyl, trifluoromethyl, carbamoyl, N-lower $(C_{1-4})$ alkylcarbamoyl and N,N-di-lower $(C_{1-4})$ alkylcarbamoyl; $R^3$ is hydrogen, methyl, acetyl or methoxycarbonyl; and A is ethylene or a hydrocarbon chain of the formula:

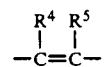

wherein $R^4$ and $R^5$ are independently hydrogen, $C_{1-8}$ alkyl group, or phenyl unsubstituted or substituted with halogen or lower $(C_{1-4})$ alkoxy.

23. A compound according to claim 22, wherein $R^1$ is a $C_{3-5}$ alkyl group.

24. A compound according to claim 22, wherein $R^2$ is a benzyl group unsubstituted or substituted with halogen.

25. A compound according to claim 22, wherein $R^3$ is hydrogen.

26. A compound according to claim 22, wherein A is ethylene or a hydrocarbon chain of the formula:

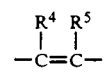

wherein $R^4$ and $R^5$ are independently hydrogen, $C_{1-4}$ alkyl or phenyl unsubstituted or substituted with lower $(C_{1-4})$ alkoxy.

27. A compound according to claim 1, which is 1-benzyl-6-(4-methoxyphenyl)-3-propyl-1,2,3,4-tetrahydro5H-imidazo [2',1':5,1]pyrazolo[3,4-d]pyrimidine-2,4-dione.

28. A compound according to claim 1, which is 1-benzyl-6-(4-chlorophenyl)-3-propyl-1,2,3,4-tetrahydro-5H-imidazo [2',1':5,1]pyrazolo[3,4-d]pyrimidine-2,4-dione.

29. A compound according to claim 1, which is 1-benzyl-6-butyl-3-propyl-1,2,3,4-tetrahydro-5H-imidazo [2',1':5,1]pyrazolo[3,4-d]pyrimidine-2,4-dione.

30. A compound according to claim 1, which is 1-benzyl-3-propyl-6-phenyl-1,2,3,4-tetrahydro-5H-imidazo [2',1':5,1]pyrazolo[3,4-d]pyrimidine-2,4-dione.

31. A compound according to claim 1, which is 1-benzyl-7-dimethylaminomethyl-3-propyl-1,2,3,4-tetrahydro-5H-imidazo [2',1':5,1]pyrazolo[3,4-d]pyrimidine-2,4-dione.

32. A compound according to claim 1 in a form of a pharmacologically acceptable salt.

33. A pharmaceutical composition suitable for antagonizing adenosine which comprises (a) as the active ingredient, an amount effective to antagonize adenosine of a compound according to claim 1 or a salt thereof and (b) a pharmaceutically acceptable carrier, excipient or diluent therefor.

34. A method for antagonizing adenosine in a mammal, which comprises administering to said mammal an amount effective to antagonize adenosine of a compound according to claim 1 or a salt thereof.

* * * * *